US012727968B2

(12) United States Patent
Grande et al.

(10) Patent No.: US 12,727,968 B2
(45) Date of Patent: Sep. 8, 2026

(54) ORTHODONTIC DEVICES AND METHODS FOR USING THOSE DEVICES

(71) Applicant: Ormco Corporation, Orange, CA (US)

(72) Inventors: Jessica Elivier Grande, Placentia, CA (US); Sammel Shahrier Alauddin, Rancho Cucamonga, CA (US)

(73) Assignee: Ormco Corporation, Brea, CA (US)

( * ) Notice: Subject to any disclaimer, the term of this patent is extended or adjusted under 35 U.S.C. 154(b) by 794 days.

(21) Appl. No.: 18/147,808

(22) Filed: Dec. 29, 2022

(65) Prior Publication Data

US 2023/0200943 A1 Jun. 29, 2023

Related U.S. Application Data

(62) Division of application No. 16/272,105, filed on Feb. 11, 2019, now abandoned.

(Continued)

(51) Int. Cl.

*A61C 7/02* (2006.01)
*A61C 7/08* (2006.01)

(Continued)

(52) U.S. Cl.

CPC ................ *A61C 7/023* (2013.01); *A61C 7/02* (2013.01); *A61C 7/08* (2013.01); *A61C 7/146* (2013.01);

(Continued)

(58) Field of Classification Search

CPC .. A61C 7/00; A61C 7/02; A61C 7/023; A61C 7/08; A61C 7/146; A61C 7/20; A61C 7/145

See application file for complete search history.

(56) References Cited

U.S. PATENT DOCUMENTS 3,949,477 A 4/1976 Cohen et al.
5,205,734 A 4/1993 Marangoni et al.

(Continued)

FOREIGN PATENT DOCUMENTS

CN 101868563 A 10/2010
CN 103610598 B 12/2015

(Continued)

OTHER PUBLICATIONS

International Searching Authority, Invitation to Pay Additional Fees in corresponding International Patent Application No. PCT/US2019/017277 dated Apr. 23, 2019.

(Continued)

*Primary Examiner* — Yogesh P Patel
(74) *Attorney, Agent, or Firm* — Firm Foundation IP LLC

(57) ABSTRACT

A device for use by a clinician includes a tip structure that is configured to extend from a handle and to be inserted into a patient's mouth and at least one light source that is capable of emitting incoherent actinic radiation from the device. The light source is on the tip structure or within the handle. A light device includes a shell that is configured to engage an orthodontic bracket while the orthodontic bracket is attached to a tooth and at least one light source is embedded in the shell and is capable of emitting incoherent actinic radiation. A method of debonding an orthodontic appliance from a tooth includes exposing an adhesive secured to the tooth to incoherent actinic radiation that reduces a bond strength of at least a portion of the adhesive and separating the orthodontic appliance from the tooth at the portion of the adhesive having reduced bond strength.

25 Claims, 19 Drawing Sheets

Related U.S. Application Data

(60) Provisional application No. 62/628,577, filed on Feb. 9, 2018.

(51) Int. Cl.
*A61C 7/14* (2006.01)
*A61C 13/15* (2006.01)
*A61C 7/20* (2006.01)
*A61N 5/06* (2006.01)

(52) U.S. Cl.
CPC ............ *A61C 19/004* (2013.01); *A61C 7/145* (2013.01); *A61C 7/20* (2013.01); *A61N 2005/0606* (2013.01)

(56) References Cited

U.S. PATENT DOCUMENTS

| | | | | |
|---|---|---|---|---|
| 5,320,532 A * | 6/1994 | Farzin-Nia | A61C 17/20 433/119 |
| 5,415,543 A | 5/1995 | Rozmajzl, Jr. | |
| 6,200,134 B1 * | 3/2001 | Kovac | A61C 19/004 433/29 |
| 7,622,550 B2 | 11/2009 | Cha et al. | |
| 7,776,940 B2 | 8/2010 | Kalgutkar et al. | |
| 8,337,201 B1 | 12/2012 | Mace | |
| 8,563,117 B2 | 10/2013 | Messersmith et al. | |
| 9,072,572 B2 | 7/2015 | Gill et al. | |
| 10,610,458 B2 | 4/2020 | Grande et al. | |
| 11,259,994 B2 | 3/2022 | Grande et al. | |
| 12,357,543 B2 | 7/2025 | Grande et al. | |
| 2004/0120162 A1 | 6/2004 | Tsimerman et al. | |
| 2005/0215034 A1 | 9/2005 | Vandroux et al. | |
| 2005/0282102 A1 | 12/2005 | Kert | |
| 2006/0064864 A1 | 3/2006 | Meissner et al. | |
| 2007/0054230 A1 | 3/2007 | Brezniak | |
| 2007/0141524 A1 * | 6/2007 | Brennan | A61C 7/16 433/9 |
| 2008/0011416 A1 | 1/2008 | DeMeter | |
| 2008/0032252 A1 | 2/2008 | Hayman et al. | |
| 2013/0157212 A1 | 6/2013 | Hibst et al. | |
| 2013/0228735 A1 | 9/2013 | Higuchi et al. | |
| 2014/0315142 A1 | 10/2014 | Montgomery | |
| 2016/0160097 A1 | 6/2016 | Waite et al. | |
| 2016/0302888 A1 | 10/2016 | García Acosta et al. | |
| 2017/0217999 A1 | 8/2017 | Ahn et al. | |
| 2019/0076334 A1 * | 3/2019 | Alauddin | C08L 33/12 |

FOREIGN PATENT DOCUMENTS

| | | | |
|---|---|---|---|
| EP | 1639960 B1 | 5/2009 |
| WO | 2007045249 A1 | 4/2007 |
| WO | 2017132463 A1 | 8/2017 |
| WO | 2017132484 A1 | 8/2017 |

OTHER PUBLICATIONS

International Searching Authority, International Search Report and Written Opinion in corresponding PCT Application No. PCT/US2019/017277 dated Jun. 14, 2019.

PCT Office, International Preliminary Report on Patentability issued in PCT/US2019/017277 mailed on Aug. 11, 2020.

European Patent Office, Examination Report issued in EP 19707545.0 dated Aug. 13, 2021.

European Patent Office, Examination Report issued in EP 19707545.0 dated Apr. 21, 2022.

U.S. Patent and Trademark Office, Non-Final Office Action issued in corresponding U.S. Appl. No. 16/272,105 dated Sep. 29, 2022.

European Patent Office, Examination Report issued in EP 19707545.0 dated Feb. 14, 2023.

Shafiq et al., "Bioinspired Underwater Bonding and Debonding on Demand," 51 Angew. Chem. Int. Ed. 4332-35 (2012).

Dental Tribune International, "Mussels help researchers develop tougher restorative product: Dental Tribune Amerca," Sep. 6, 2017.

Internatonal Searching Authority, International Search Report and Written Opinion in corresponding PCT/US2018/049937 dated Jan. 8, 2019.

Sang-Bae Lee et al., "Cathechol-Functionalized Synthetic Polymer as a Dental Adhesive to Contaminated Dentin Surface for a Composite Restoration", BIOMACROMOLECULES, vol. 16, No. 8, Jul. 31, 2015, pp. 2265-2275.

Sungbaek Seo et al., "Significant Performance Enhancement of Polymer Resins by Bioinspired Dynamic Bonding", Advanced Materials, vol. 29, No. 39, Aug. 18, 2017.

Theodore Eliades: "Orthodontic materials research and applications: Part 1. Current status and projected future developments in bonding and adhesives", American Journal of Orthodontics and Dentofacial Orthopedics, vol. 130, No. 4, 2006, pp. 445-451.

Zhang Hong et al., "Mussel-inspired hyperbranched poly(amino ester) polymer as strong wet tissue adhesive", BIOMATERIALS, vol. 35, No. 2, 2014, pp. 711-719.

U.S. Department of the Interior, Reclamation: Managing Water in the West, Technical Memorandum No. MERL_2013-43, "Review of Mussel Adhesion Mechanism and Scoping Study," Aug. 2013.

Chinese Patent Office, Office Action issued in CN 201880058425.4 dated Jun. 1, 2022.

Li Zhiyu, Medicinal Chemistry, Southeast University Press, pp. 74-75, Dec. 31, 2006.

Chinese Patent Office, Office Action issued in 201880058425.4 dated Jan. 4, 2023.

Australian Patent Office, Examination Report issued in Australian Patent App. No. 2018327265 dated Apr. 27, 2023.

Australian Patent Office, Examination Report issued in AU 2018327265 dated Nov. 3, 2022.

Canadian Patent Office, Office Action issued in CA 3074692 dated Apr. 5, 2024.

European Patent Office, Examination Report issued in EP 18782240 dated Sep. 22, 2021.

Japanese Patent Office, Office Action issued in JP 2023075756 dated Jun. 10, 2024.

Japanese Patent Office, Office Action issued in JP 2020513898 dated September 5, 202.

Japanese Patent Office, Office Action issued in JP 2020513898 dated Jan. 30, 2023.

European Patent Office, Notice of Allowance issued in EP 18782240 dated Jan. 30, 2025.

European Patent Office, Extended Search Report and Written Opinion issued in EP 25188175.1 dated Oct. 17, 2025.

Canadian Patent Office, Office Action issued in CA 3074692, dated Oct. 24, 2025.

* cited by examiner

ORTHODONTIC DEVICES AND METHODS FOR USING THOSE DEVICES

CROSS REFERENCE

This application is a Divisional of U.S. patent application Ser. No. 16/272,105 filed Feb. 11, 2019 (pending), which claims the benefit of priority to U.S. Provisional Patent Application Ser. No. 62/628,577 filed on Feb. 9, 2018, the disclosures of which are expressly incorporated by reference herein in their entirety.

FIELD

The present invention is generally related to the field of orthodontic devices and methods of using those devices.

BACKGROUND

Current orthodontic treatment with orthodontic brackets or other devices that may be attached to the patient's teeth may require the enamel to be prepared prior to attachment of the device to the tooth. Preparation of the tooth surface may be through a series of steps including cleaning, acid etching, and sealing, with intermediate rinse and dry steps, before the clinician may apply an adhesive. For example, to bond a bracket to tooth enamel, each tooth is first cleaned with a slurry of abrasive, such as pumice, to remove pellicle from the enamel. Then, after rinsing and drying the cleaned surface, a phosphoric acid etchant is carefully placed on the surface locations of the tooth to which the clinician desires to attach the orthodontic device. The acid etching step demineralizes the enamel surface and removes a layer of approximately 30 μm or so of hydroxyapatite from the enamel rods. After between 30 and 90 seconds of etch time, the etchant is rinsed away with a water spray and a high flow evacuator. In this way, etching provides a porous structure.

Following the drying step after etching, a sealant (e.g., Ortho Solo™ sealant) is applied to the etched surface. The sealant may penetrate the porous, acid etched surface. Once the sealant cures, a mechanical interlock is created between the tooth and the sealant. An adhesive (e.g., Enlight) and the bracket may be pressed onto the sealed surface with the adhesive between the bracket and the sealant. The adhesive may be a composite resin paste adhesive that includes a mixture of methacrylate monomers, a photo-initiator, and a glass/hydroxyapatite powder. Once the adhesive cures, it secures the bracket to the sealant. This bonding arrangement results in a sandwich-like construction with the sealant and the adhesive sandwiched between the tooth surface and the orthodontic bracket. This procedure and bonding arrangement is then repeated for each tooth that will receive an orthodontic device and so, in the case of orthodontic brackets and molar tubes, this may involve 28 teeth per patient.

The current preparation process has many drawbacks. From the perspective of the clinician, it is a manually time-intensive process. It is not surprising that office chair time during the entire bonding procedure is lengthy. Overall, bonding orthodontic brackets to teeth is costly. From the patient's perspective, the process is uncomfortable and enamel removal is often irreversible due to the difficulty of remineralizing dental hard tissues. Thus, the tooth surface may be permanently compromised by acid etching. Certain patients may have an allergic reaction to the etchant. Liquid etchant may flow to the gingiva where it may irritate the soft tissue. Gel etchant, despite allowing more precise placement, requires skillful application and is more difficult to remove. In either application, when the etchant must be rinsed away, care must be taken not to splash or wash the etchant in a manner that may harm the patient or clinician, but the rinsing must be thorough so that the etching reaction is terminated and there is no residual acid or mineral debris that hinders the mechanical interlock between the tooth and the device.

After orthodontic treatment is complete, the clinician must remove the orthodontic bracket from each tooth. This debonding process requires the clinician to break the bond formed during the bonding process. Mechanically fracturing the bond may require significant skill on the part of the clinician if the patient is to avoid pain. To debond orthodontic brackets, an orthodontist or a clinician may use a tool, such as a pair of pliers, to grip the bracket while it is bonded to the patient's tooth. With twisting motion, shear forces are applied to the bracket and the tooth. Once the applied shear force exceeds the adhesive bond strength, the bracket separates from the tooth. Even if done properly, debonding with a pair of pliers or a similar tool is disconcerting and uncomfortable for the patient. And, even with orthodontic brackets that include design features for easier debonding, considerable adhesive/sealant residue may be left on the tooth surface after removal of the bracket. This residue must be mechanically removed with a dental bur, which is also an extremely uncomfortable process for the patient and is tedious for the clinician.

Therefore, a need exists for orthodontic devices, adhesives, and methods of using those devices and adhesives to reduce issues associated with debonding orthodontic devices from teeth.

SUMMARY

The present invention overcomes the foregoing and other shortcomings and drawbacks of orthodontic devices, adhesives, and methods of using those devices and adhesives heretofore known for use in orthodontic treatment. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a device for use by a clinician in orthodontics comprises a tip structure that is configured to extend from a handle and to be inserted into a patient's mouth and at least one light source that is capable of emitting incoherent actinic radiation from the device. The light source is on the tip structure or within the handle.

In one embodiment, the device further includes a sonic or ultrasonic generator coupled to the tip structure and configured to vibrate the tip structure.

In one embodiment the device further includes the handle and a housing defines the handle and the sonic or ultrasonic generator is in the housing.

In one embodiment, the at least one light source emits light in at least one of an IR spectrum, an NIR spectrum, and an UV spectrum to irradiate a cured adhesive within the patient's mouth.

In one embodiment, the at least one light source includes a first light source for the IR or NIR spectrums and a second light source for the UV spectrum.

In one embodiment, the first light source and the second light source are capable of being simultaneously activated so that the device emits light in each of the IR or NIR spectrums and the UV spectrum.

In one embodiment, the device further includes a source of blue light that is capable of emitting light in a blue portion of a visible light spectrum to cure an adhesive within the patient's mouth.

In one embodiment, the at least one light source is capable of producing an irradiance of 50 mW per $cm^2$ to 250 mW per $cm^2$.

In one embodiment, the at least one light source is capable of producing an irradiance up to an amount that does not heat a cured adhesive within a patient's mouth.

In one embodiment, the handle includes a socket and the tip structure is one of a set of a plurality of different tip structures, and each of the tip structures in the set is capable of being removably coupled to the handle in the socket.

In one embodiment, the tip structure is L-shaped and includes a first leg and a second leg extending generally perpendicularly from the first leg.

In one embodiment, the tip structure includes a shield that is configured to be positioned between adjacent teeth and to block light emitted from the device from impinging upon at least one tooth.

In one embodiment, the tip structure includes a bite plate and a sidewall that is configured to face a surface of the patient's teeth and the at least one light source is positioned in the sidewall, the tip structure being configured to irradiate an entire arch of the patient's mouth.

In one embodiment, the tip structure is configured to capture an orthodontic appliance when it separates from a tooth and prevents the orthodontic appliance from contacting a portion of the patient's mouth.

In one embodiment, the tip structure is configured to apply a debonding force to the orthodontic appliance.

In one embodiment, the tip structure includes a shell configured to physically contact the orthodontic appliance. In one embodiment, the shell includes a cavity defined in part by opposing projections. In one embodiment, the shell includes at least one projection capable of contacting and applying a tensile force on the orthodontic appliance.

In one embodiment, the tip structure includes a tool for contacting the orthodontic appliance and the at least one light source is adjacent the tool.

In one embodiment, the device further includes a fluid reservoir coupled to the housing.

In one embodiment, the housing includes a port fluidly coupled to the fluid reservoir, the device being configured to eject fluid from the fluid reservoir from the port.

In one embodiment, the port is adjacent the tool.

In accordance with the principles of the present invention, a light device comprises a shell that is configured to engage an orthodontic bracket while the orthodontic bracket is attached to a tooth, and at least one light source is embedded in the shell and is capable of emitting incoherent actinic radiation.

In one embodiment, the shell defines a cavity configured to receive the orthodontic bracket and the at least one light source is configured to irradiate the cavity.

In one embodiment, the cavity includes opposing projections that are configured to create an interference fit with the orthodontic bracket when the bracket is in the cavity.

In one embodiment, the shell further includes a U-shaped portion that is configured to fit over an occlusal edge of the tooth.

In one embodiment, the at least one light source emits light in at least one of an IR spectrum, an NIR spectrum, and an UV spectrum to irradiate a cured adhesive within the patient's mouth.

In one embodiment, the at least one light source includes a first light source for the IR or NIR spectrums and a second light source for the UV spectrum.

In one embodiment, the light device further comprises a source of blue light that is capable of emitting light in a blue portion of a visible light spectrum to cure an adhesive with the patient's mouth.

In one embodiment, the at least one light source is capable of producing an irradiance of 50 mW per $cm^2$ to 250 mW per $cm^2$.

In one embodiment, the at least one light source is capable of producing an irradiance that does not heat a cured adhesive within the patient's mouth.

In accordance with the principles of the present invention, a method of debonding an orthodontic appliance from a tooth comprises exposing an adhesive secured to the tooth to incoherent actinic radiation that reduces a bond strength of at least a portion of the adhesive and separating the orthodontic appliance from the tooth at the portion of the adhesive having reduced bond strength.

In one embodiment, exposing the adhesive to actinic radiation includes exposing a plurality of orthodontic appliances simultaneously to the actinic radiation.

In one embodiment, exposing the adhesive to actinic radiation includes exposing the adhesive to radiation in at least one of an IR spectrum, an NIR spectrum, and an UV spectrum.

In one embodiment, exposing the adhesive to actinic radiation includes exposing the adhesive to actinic radiation in each of an IR spectrum and a UV spectrum or in each of an NIR spectrum and a UV spectrum.

In one embodiment, prior to exposing, the method further comprises applying the adhesive to one of the tooth and the orthodontic appliance, affixing the orthodontic appliance to the tooth via the adhesive, and exposing the adhesive to a different spectrum of radiation from the incoherent actinic radiation to bond the orthodontic appliance to the tooth.

In one embodiment, following exposing the adhesive to the actinic radiation, the method further comprises reorienting the orthodontic appliance relative to the tooth, and after reorienting, repeating the exposing of the adhesive to the different spectrum of radiation to bond the orthodontic appliance in a different orientation on the tooth.

In one embodiment, separating includes generating sonic or ultrasonic vibrations and exposing the adhesive to the vibrations.

In one embodiment, exposing the adhesive to the vibrations occurs simultaneously with exposing the adhesive to the actinic radiation.

In one embodiment, during exposing the adhesive to the vibrations, the method further comprises applying a fluid to the tooth.

In one embodiment, separating occurs during exposing.

In one embodiment, separating occurs under the influence of gravity.

In one embodiment, the method further comprises impinging a fluid on the tooth during separating.

In one embodiment, separating includes applying one or both of a tensile force or a shear force on the adhesive.

In one embodiment, applying includes pulling on one or both of an orthodontic bracket or an archwire to separate the orthodontic bracket from the tooth.

In one embodiment, prior to exposing the method further comprises coupling a shell to the orthodontic appliance.

In one embodiment, the shell defines a cavity and coupling includes placing the orthodontic appliance into the cavity.

BRIEF DESCRIPTION OF THE DRAWINGS

The accompanying drawings, which are incorporated in and constitute a part of this specification, illustrate embodiments of the invention and, together with a detailed description given below, serve to explain the principles of the invention.

DETAILED DESCRIPTION

Figure 1:
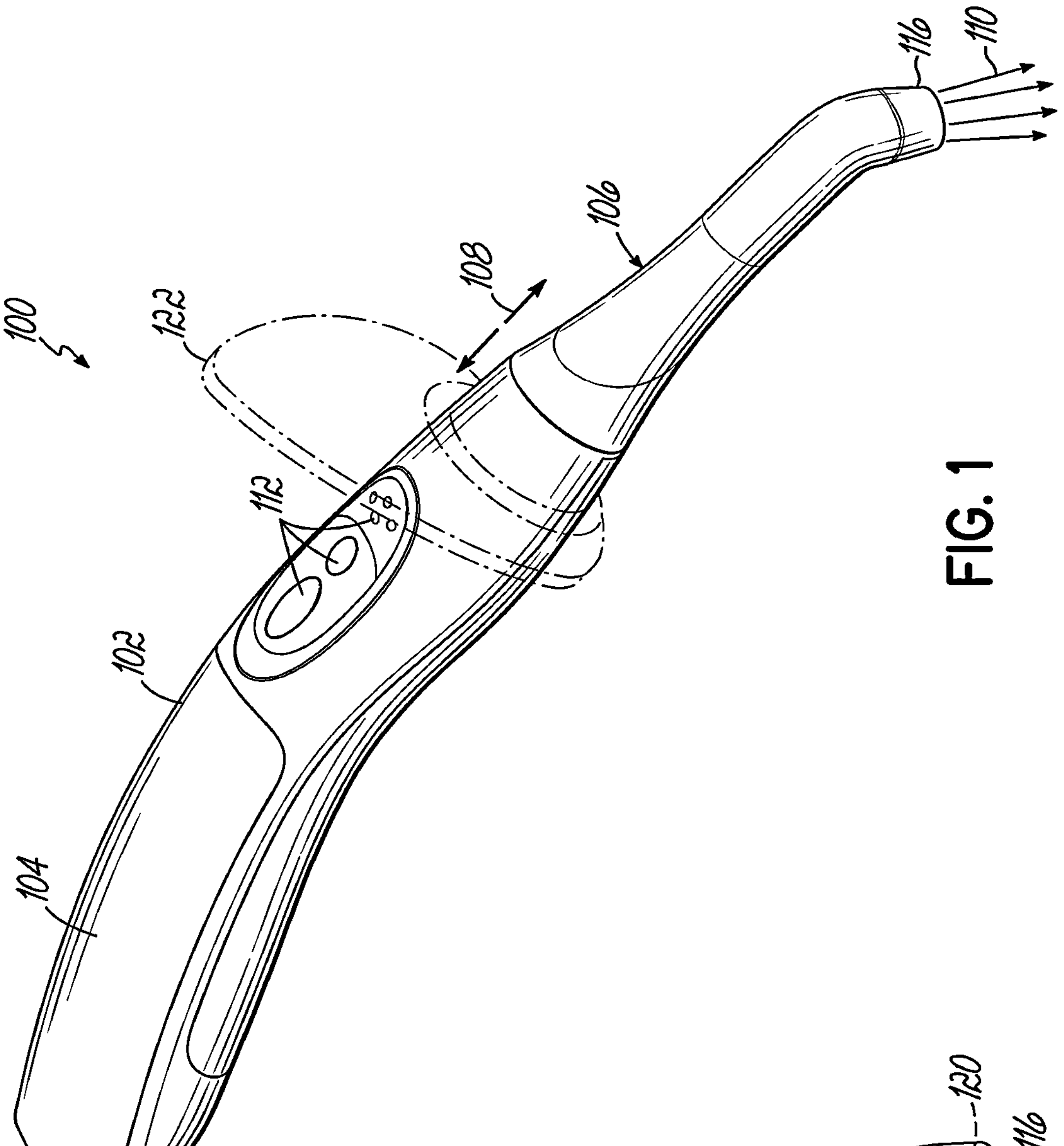
FIG. 1 is a perspective view of a light device according to one embodiment of the invention.

With reference to FIG. 1, an exemplary embodiment of a light device 100 of the present invention is shown. Any single one of the light devices described herein may be used for irradiating an adhesive with light of various effective wavelengths as described below. In addition, the light devices may emit light while simultaneously producing mechanical vibration. By way of example only, the light device 100 may be used in orthodontic procedures in which an adhesive is used to bond an orthodontic appliance to one or more of the patient's teeth. The adhesive is responsive to actinic radiation emitted from the light device 100. In that regard, the clinician utilizes the light device 100 so that the clinician can more easily separate the orthodontic appliance from the tooth. Light from the light device 100 may break chemical bonds within the atomic structure of at least a portion of the adhesive. A working theory is that as the bonds break, the mechanical strength of the adhesive is reduced, which makes the adhesive more susceptible to intentional application of an applied force to remove the orthodontic appliance from the tooth. Where the adhesive includes a polymer, weakening the adhesive may be by a depolymerization process. The weakening process alternatively may be described as a decomposition process. In one embodiment, depolymerization reduces a bond strength between an orthodontic appliance and a tooth surface. Where the light device 100 also produces mechanical vibration, the simultaneous combination of light and vibrational energy may cause the orthodontic appliance to dislodge from the tooth. According to another embodiment, the clinician may utilize the light device 100 to both bond and debond an orthodontic appliance from a tooth. In that regard, the light device 100 may have a dual mode capability.

To these and other ends, as shown in FIG. 1, the light device 100 includes a housing 102, which forms a handle 104. The clinician may grasp the handle 104 to utilize the light device 100 during patient treatment. The clinician may removably couple a tip structure 106 to the handle 104 at one end according to the arrow 108 in FIG. 1. Although not shown, the handle 104 may include a socket that removably receives the tip structure 106. Light (schematically shown with arrows 110) is emitted from the tip structure 106 when positioned in a patient's mouth. The tip structure 106 is shown separated from the handle in FIG. 2 and may therefore be autoclaved separately from the handle 104 or the tip structure 106 may be a disposable item. One tip structure 106 may be utilized per patient per visit. This advantageously eliminates the need for sterilization between patients. As is described below, the clinician may couple other tip structures to the handle 104 depending on the number of teeth and orientation of a light source relative to the orthodontic appliance during irradiating of selected adhesive bonds. Thus, the handle 104 may be a universal component in a set of orthodontic devices with one handle and multiple, interchangeable tip structures described herein.

The clinician may cause the light device 100 to selectively generate and emit electromagnetic radiation (illustrated by arrows 110) from the tip structure 106 to irradiate adhesive bonds. To that end, the light device 100 also includes suitable control electronics (not shown) with at least one external control 112 that may include a plurality of buttons, switches, or other suitable manual controls for controlling the light device 100. Selecting one of the external controls 112 permits the clinician to control the emission of radiation from the tip structure 106. The controls 112 may include on-off controls as well as means for selection of one or more wavelengths of light or types of light (e.g., ultraviolet (UV) spectrum, a blue portion of a visible light spectrum, infrared (IR) spectrum, and near infrared (NIR) spectrum) that are emitted from the tip structure 106. Each of these spectrums of light may produce a different effect on an adhesive. A combination of wavelengths from the UV and IR/NIR spectrums may also be emitted from the light device 100. The clinician may therefore select a particular result by selecting a wavelength of light to be emitted from the light device 100 via the controls 112. Other controls 112 may include a timer and wattage selection. As is described below in conjunction with FIGS. 9A-15B, the clinician may insert the tip structure 106 into the patient's mouth to a location at which an adhesive is located and then operate the external controls 112 so that the light device 100 emits radiation from the tip structure 106 toward an adhesive.

With continued reference to FIG. 1, in one exemplary embodiment, a shield 122 is coupled to the handle 104 and may alternatively be coupled to the tip structure 106. The shield 122 may be transparent to visible light but may attenuate or block radiation that is emitted from the tip structure 106 and that reflects from the patient's mouth toward the clinician. As such, the clinician may be able to view the treatment area in the patient's mouth through the shield 122 though any radiation that strikes the patient's teeth and is reflected or scattered in a direction toward the clinician may be at least partially blocked by the shield 122.

Figure 2:
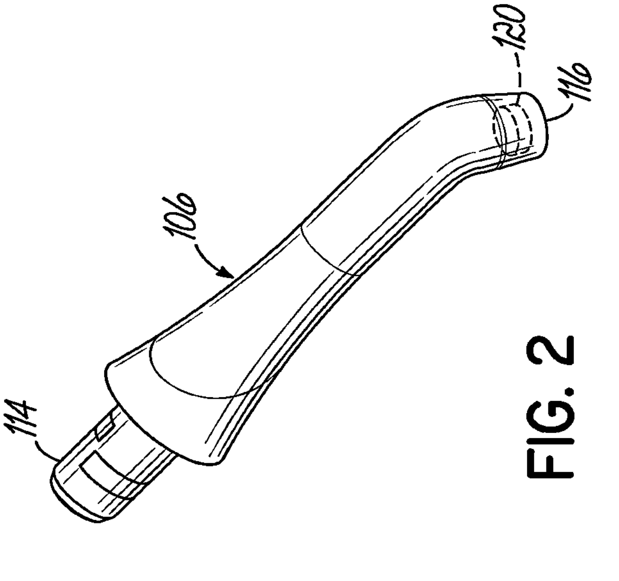
FIG. 2 is a perspective view of a tip structure of the light device shown in FIG. 1.

With reference now to FIG. 2, in one embodiment, the tip structure 106 includes a proximal end 114 at which the tip structure 106 is removably coupled with the handle 104 (FIG. 1) and a distal end 116 that is placed within the mouth of a patient for irradiating an adhesive. The distal end 116 may include a light source 120. By way of example, the light source may include one or more LEDs, one or more polymer-light emitting electrochemical cells (LECs). LEDs are commercially available from Osram Sylvania of Wilmington, Massachusetts; Excelitas Technologies Corp. of Waltham, Massachusetts; and Kodenshi Corp. of South Korea. These LEDs have a peak emission wavelength of from 810 nm to 860 nm. For example, Osram manufactures the SFH 4253 LED with a peak emission wavelength of 860 nm. The LECs may be designed in numerous shapes and may additionally use quantum dots to select specific wavelengths to be applied. The light source 120 produces incoherent radiation and so, in one embodiment, is not a laser. There may be one light source for each of the spectrums selectable by the clinician. The clinician may operate at least one of the light sources 120 at a time to selectively emit one or more wavelengths of light or light in one or more light spectrums.

Alternatively, the light source 120 may be remote from the tip structure 106. For example, the light source 120 may be housed within the handle 104. Waveguides may couple the light source 120 in the handle 104 through the tip structure 106 so that light is transported from the handle 104 through the tip structure 106 and is emitted from the distal end 116. Even further, the light source 120 may be remote from the light device 100, that is, not in the handle 104, though the light device 100 may be coupled to the remote light source via one or more waveguides, such as a fiber optic, that extends from the handle 104 to the remote source.

The light source 120 is controllable via the controls 112 to emit light in at least one of the IR spectrum (i.e., wavelengths of about 700 nm to about 1 mm), NIR spectrum (i.e., wavelengths of about 780 nm to about 2500 nm), a blue portion of the visible light spectrum (e.g., wavelengths of 450 nm to 495 nm), and the UV spectrum (i.e., wavelengths of about 10 nm to about 400 nm). The light source 120 may include separate sources for each of the IR, NIR, and UV spectrums. For example, the light source 120 may be a plurality of LEDs with different LEDs for any two or all three of the IR spectrum, NIR spectrum, and the UV spectrum.

Although not shown in FIGS. 1 and 2, the light device 100 may be coupled to a charger base during nonuse so that a power source (e.g., a battery) within the light device 100, such as within the handle 104, may be recharged. Exemplary charger base electronics as well as additional features of a dental light device are further described in commonly owned U.S. Pat. No. 9,072,572, which is incorporated by reference herein in its entirety.

The light device 100 may be capable of producing light of sufficient total radiant flux to irradiate an adhesive and reduce its bond strength. Total radiant flux is equal to the total radiated power output integrated over the entire emission spectrum of the light source and over all spatial orientations. In other words, total radiant flux is the total amount of light energy emanating from the light source each second and is measured in Joules per second or Watts (W). With reference to the LEDs described herein, for example, an Osram FH 4253 LED with a peak emission wavelength of 860 nm that produces about 10 mW at an applied voltage of 1.45 V with a lens area of about 0.045 $cm^2$ outputs a dosage sufficient to break chemical bonds when the adhesive is exposed for about 10 minutes when the LED is held at a distance of 0.5 cm to 1 cm. And, as another example, LEDs that produce a wavelength of 940 nm at 2.75 W (measured at a distance of 0.5 cm to 1 cm) provide a dosage sufficient to break chemical bonds in about 30 seconds, for example, from 26 seconds to 34 seconds, as is described below.

This power output translates into dosage measured in energy per unit area (e.g., Joules per $cm^2$). The dosage is the product of the irradiance and exposure time as applied to a surface of the adhesive at the tooth-adhesive interface, or at the bracket-adhesive interface. This may be represented by the equation:

$$\text{Dosage}\left(\frac{\text{J}}{\text{cm}^2}\right) = \text{Irradiance}\left(\frac{\text{mW}}{\text{cm}^2}\right) * \text{Exposure time (s)}$$

where $$\text{Irradiance}\left(\frac{\text{mW}}{\text{cm}^2}\right) = \frac{\text{Radiant Flux (mW)}}{\text{Area of recieving surface }(\text{cm}^2)}$$

The light device 100 may include an aperture or window (not shown) through which light from the light source exits the device. The aperture limits the output of the light source to a specific direction so the radiant flux in the above equation may reflect the total radiant flux of the light source as portioned by the aperture. Although not indicated in the equations, a distance between the receiving surface and the light device 100 also plays a role in the determining the radiant flux at the receiving surface relative to the total radiant flux because light may be lost, e.g., absorbed, between the light source and the receiving surface. The reduction in bond strength from exposure to the selected light may occur at a rate sufficient to permit a clinician to remove an appliance bonded to the tooth after a few minutes (e.g., less than 10 minutes) or even a few seconds (e.g., less than 60 seconds). Removal of the appliance may occur without patient pain or discomfort. By way of example only, the appliance may fall off the patient's tooth under the force of gravity after the bond between the tooth and the appliance is exposed to radiation produced by the light device 100. That is, no force other than gravity is applied to the appliance. Alternatively, as is described below with reference to FIGS. 15A-20B, the clinician may apply an external mechanical force (e.g., a shear force), such as with a tool or finger, to remove the orthodontic appliance after the bond is sufficiently weakened.

While the selection of a particular range of light wavelengths promotes debonding of the orthodontic appliance by a depolymerization process, the irradiance of that selected light source may at least partially determine the rate at which the strength of the adhesive bond decreases. In an exemplary embodiment, the light device 100 is capable of an irradiance of at least about 77 mW per $cm^2$ to about 200 mW per $cm^2$ over the course of a few seconds or a few minutes (less than 10 minutes). Embodiments of the invention are not limited to this range of irradiance, for example, it is contemplated that an irradiance of up to 1 W per $cm^2$ is usable. Not being bound by theory, increasing the radiant flux (e.g., increasing the total radiant flux of the light source) of the light device 100 may reduce the time required to debond an orthodontic appliance from the patient's tooth. This reduction is believed to be achieved by increasing the rate of bond cleaving, and thus weakening the strength of the adhesive between the tooth and the appliance. For example, at an output power of about 3 W, it may take about 10 minutes of exposure to sufficiently reduce the bond strength of the adhesive to the point at which the clinician may remove an orthodontic appliance from the patient's teeth with only light mechanical debonding forces. These forces are less than the forces typically applied with a pair of pliers, which is at least 7 MPa. In one embodiment, the clinician activates the light device 100 to expose the adhesive 10 to light of a selected wavelength and the adhesive bond strength is reduced to less than 7 MPa in 10 minutes or less. Increasing the power output to 5 W may reduce an exposure time to 5 minutes or less. And, further increasing the output power to 15 W may sufficiently reduce the bond strength in 10 seconds or less.

As described about, the light device 100 may have dual capability, that is, the light device 100 may be utilized in both bonding and debonding of appliances to the patient's teeth with an adhesive. According to an exemplary embodiment, because the adhesive depolymerizes, high output power (e.g., 100 W or more) is not required to heat the adhesive. In that regard, the light device 100 exposes the adhesive to light in the range of 50 mW per $cm^2$ to 250 mW per $cm^2$ so that cleavage and debonding occurs at or near (within 2° C.) of normal body temperature. There is no change in viscosity of the adhesive due to a measurable temperature increase.

Figure 3A:
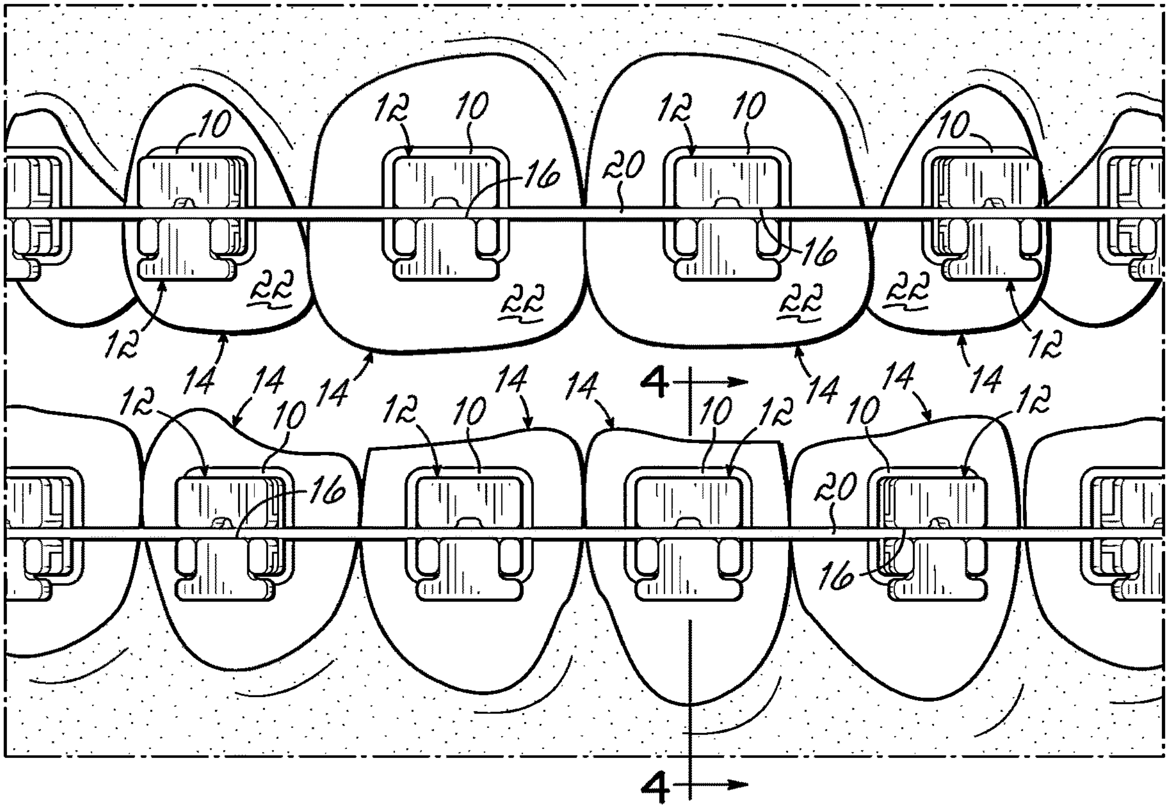
FIG. 3A shows a set of orthodontic brackets with individual brackets attached to the teeth of a patient.
Figure 4:
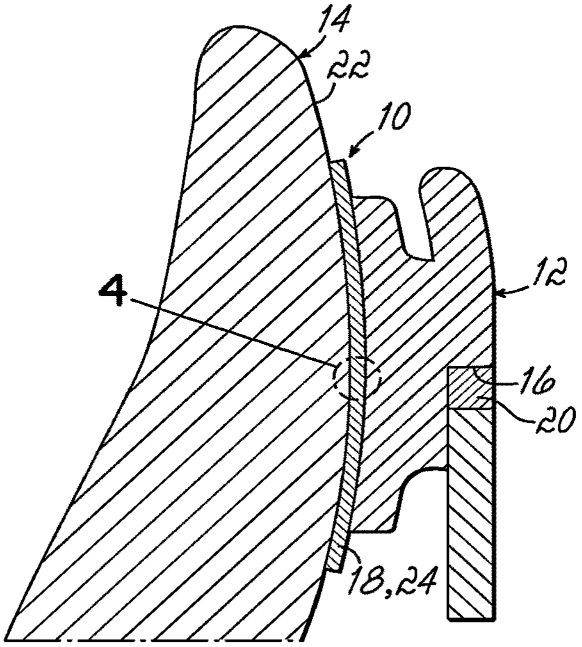
FIG. 4 is a cross-sectional view taken along section line 4-4 of FIG. 3A.

To that end, with reference now to FIGS. 3A-8, in one embodiment, a clinician may utilize an orthodontic adhesive system 10 to adhere an orthodontic device to a patient's tooth. The clinician may utilize the light devices described herein for depolymerizing at least a portion of the adhesive system 10. While depolymerization is described, it will be appreciated that other forms of decomposition of at least a portion of the adhesive may occur, that is, embodiments of the invention are not limited to breaking of bonds in a polymer. As described herein, the orthodontic adhesive system 10 includes an engineered protein. By way of example only, as shown in FIG. 3A, an orthodontic bracket 12 may be used in an orthodontic procedure. One orthodontic bracket 12 may be affixed to each of a plurality of teeth 14 with the orthodontic adhesive system 10. The orthodontic bracket 12 defines a substantially transversely disposed archwire slot 16, which receives an archwire 20. The orthodontic bracket 12 may be adhesively secured to an exterior facing surface 22 (i.e., the labial surface) of each tooth 14 with the orthodontic adhesive system 10. Although not shown in FIG. 3, the orthodontic adhesive system 10 may be between each of the orthodontic brackets 12 and the corresponding tooth 14. While brackets 12 are shown and described herein, embodiments of the present invention may be utilized to bond other orthodontic appliances to the patient's teeth. For example, the orthodontic adhesive system 10 may form attachments, shown in FIG. 3B. An aligner 60 with corresponding bulges 64 is configured to engage attachments 10 for orthodontic treatment. By way of additional example, the adhesive system 10 may be utilized to bond a lingual retainer and bite turbos, to name a few, to the patient's teeth.

With reference to FIGS. 3A-9B, the light device 100 may be utilized to at least selectively debond one or more the orthodontic brackets 12 (FIG. 3A) or attachments 10 (FIG. 3B) from a corresponding one or more of the patient's teeth 14. In one embodiment, the light device 100 may be utilized both during bonding of one bracket 12 to one of the patient's teeth 14 and during debonding of the bracket 12 from the tooth. Similarly, referring to FIG. 3B, the light device 100 may be used both during bonding of the attachment 10 to one of the patient's teeth 14 and during debonding of the attachment 10 from the tooth 14.

Figure 6:
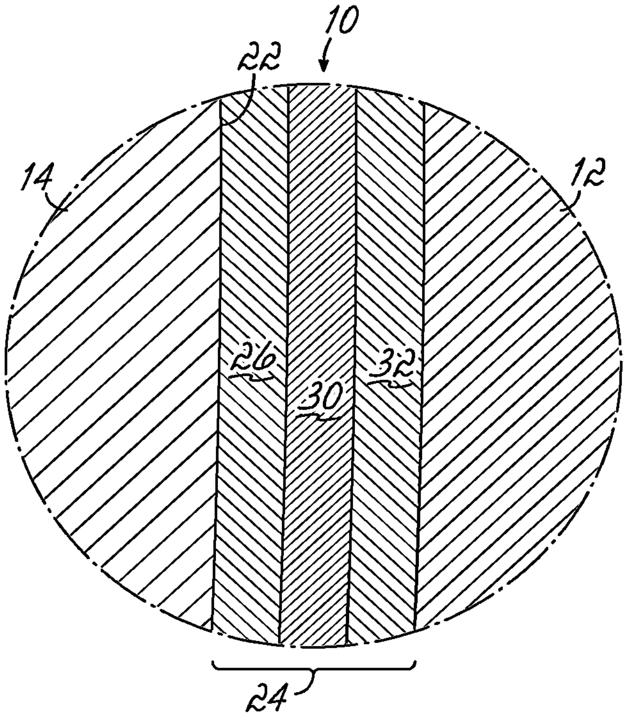
FIG. 6 is an enlarged view of an encircled area 4 of FIG. 4 according to one embodiment of the invention.
Figure 7:
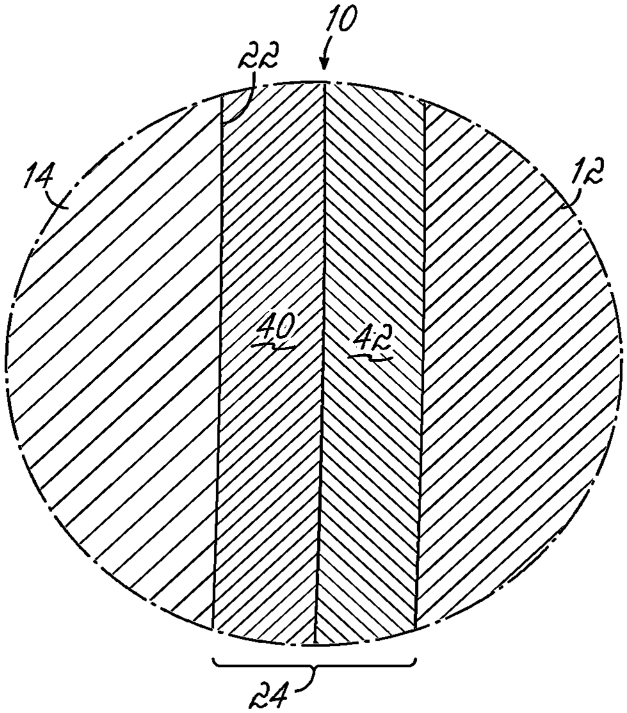
FIG. 7 is an enlarged view of the encircled area 4 of FIG. 4 according to one embodiment of the invention.
Figure 8:
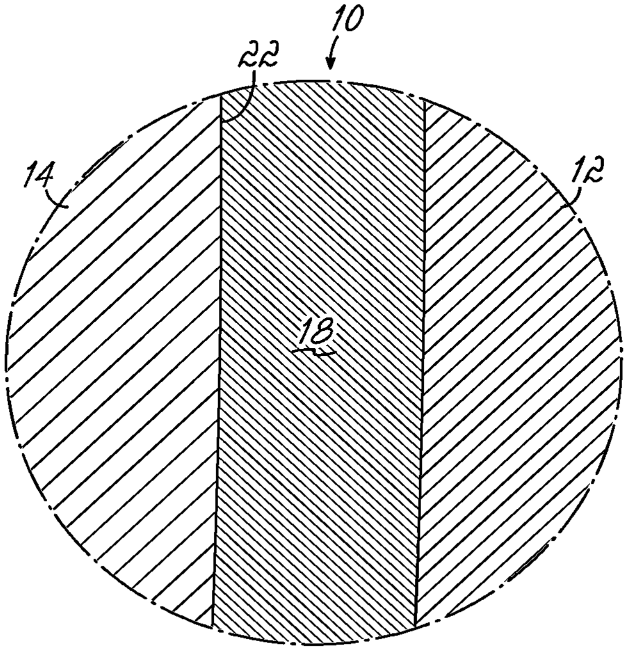
FIG. 8 is an enlarged view of the encircled area 4 of FIG. 4 according to one embodiment of the invention.

With reference to FIGS. 4-8, the orthodontic adhesive system 10 may include a single layer 18 of one or more components as is shown in FIG. 8 or a plurality of layers 24 of individual, separately-applied components, as is shown in FIGS. 4-7. While the plurality of layers 24 appear to be illustrated in approximately equal parts in FIGS. 5-7, this is not necessary. Although not shown, the plurality of layers 24 of individual, separately-applied components may be of differing dimensions and thicknesses in relation to each other. The layers 18, 24 include one or more components that are configured to bond to one of the tooth surface 22 or an orthodontic appliance 12 or form a bond between other components in a sandwich-like composite construction. An exemplary orthodontic adhesive is described in commonly owned U.S. application Ser. No. 15/699,230 which is expressly incorporated by reference herein in its entirety. Other exemplary adhesives include those disclosed in U.S. Pub. Nos. 2016/0160097 and 2017/0217999 which are each incorporated by reference herein in their entirety. When attached to respective teeth 14 with the orthodontic adhesive system 10, the brackets 12 and the archwire 20, or the aligner 60 and attachments 10, collectively provide orthodontic treatment.

The orthodontic adhesive system 10 may eliminate one or more of the tooth preparation steps. For example, the orthodontic adhesive system 10 may not require one or more of the cleaning and acid etching steps, described above, though the system 10 secures the orthodontic bracket 12 to a corresponding tooth 14 or is formed in to an attachment 10. Furthermore, the light device 100 improves removal of an orthodontic bracket 12 adhered to a tooth with the orthodontic adhesive system 10. In one aspect, embodiments of the light devices eliminate the need to apply mechanical force to debond the bracket 12 from the tooth 14, and so patients will not experience the discomfort during removal. Alternatively, the adhesive system 10 permits reduced mechanical forces in debonding when the devices described herein are applied to the adhesive system 10. Embodiments of the light devices described herein may be utilized during at least debonding of the bracket 12 from the corresponding tooth 14 or during removal of one or more of the attachments 10. Debonding may include depolymerization/decomposition of chemical bonds in one or more of the layers 24.

Following removal of the orthodontic bracket 12 or attachment 10, there will be minimal, if any, adhesive residue on the tooth 14. Embodiments of the invention will therefore also eliminate or minimalize post-removal cleaning of the teeth 14. The clinician may not need to restore the tooth surface to its pre-treatment condition and so the tooth may not suffer iatrogenic damage due to grinding or other abrasive processes. As another advantage to both the patient and clinician, the light device 100 facilitates reversible bonding and debonding of an appliance to the tooth 14. That is, a bonding network of the orthodontic adhesive system 10 is selectively activated (e.g., polymerized) with the light device 100 to bond and deactivated (e.g., depolymerized) with a light in a different spectrum from the light device 100 to debond the adhesive system 10 from the surface of the tooth 14. A clinician may then easily correct the orientation of a misplaced orthodontic appliance or attachment by selection of different wavelengths and exposing the adhesive to those wavelengths with the light device 100. In an exemplary embodiment, the light device 100 only facilitates debonding the orthodontic appliance from the tooth because the adhesive system 10 is not capable of polymerizing following depolymerization.

With reference to FIGS. 4-8, the catechol-like moiety and the functional monomer of the engineered protein adhesive of the orthodontic adhesive system 10 may be tethered together to form at least a portion of layer 18, 24 with the catechol-like moiety bonding to the tooth surface 22. This moiety may facilitate adhesion of the monomer to the tooth surface 22 in the absence of prior cleaning, etching, and drying the tooth surface 22. By eliminating one or more of these preparation steps, embodiments of the invention significantly reduce chair time. The reduction in time to bond a single bracket to a tooth may be reduced by about 80%. For example, conventional preparation and adhesive may require as much as 4 minutes per tooth. The adhesive system 10 may reduce that to about 30 seconds per tooth. A typical bonding appointment takes from 2 to 3 hours of patient commitment. In accordance with embodiments of the present invention, a clinician may bond orthodontic appliances to a patient's teeth on the same day as an initial consultation. This is not commonly practiced because of the long chair time requirements associated with bonding orthodontic appliances to the patient's teeth using conventional techniques, adhesives, and systems. Moreover, the reduction in bonding time, and chair time associated therewith, results in reduced cost for the clinician while increasing potential profitability by increasing the clinician's capacity to see more patients.

In any of the exemplary adhesive systems 10 shown in FIGS. 4-8, the monomer of the engineered protein adhesive adheres to the tooth surface 22 and forms a base onto which the orthodontic device is ultimately attached. For example, and with reference to FIG. 5, in one embodiment, the orthodontic adhesive system 10 may include four layers that collectively form the composite layer 24. In that regard, the orthodontic adhesive system 10 may include one or more separately applied layers 26, 28, 30, and 32 that collectively bond the orthodontic bracket 12 to the tooth 14. Each of the components in the layers 26, 28, 30, 32 bonds with components in the other layers and/or with the tooth 14 or the orthodontic bracket 12.

Figure 5:
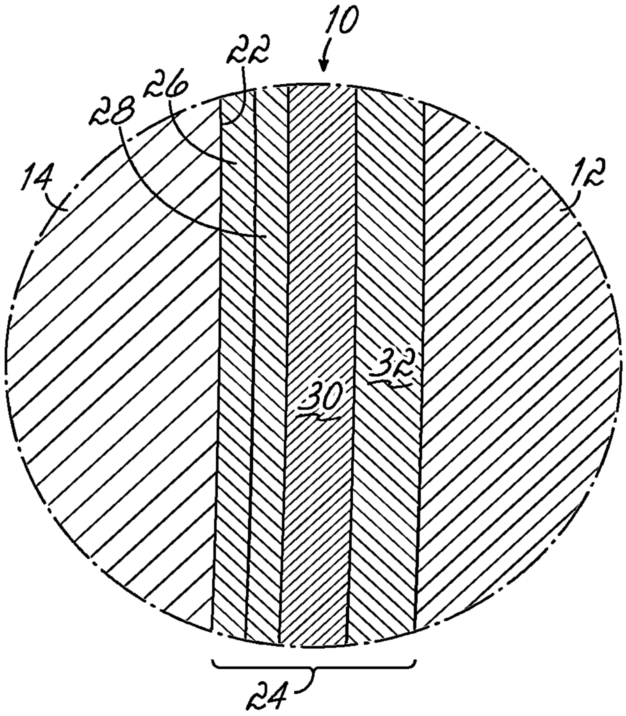
FIG. 5 is an enlarged view of an encircled area 4 of FIG. 4 according to one embodiment of the invention.

In FIG. 5, the layer 26 is in direct contact with the tooth surface 22. The layer 26 includes a monomer of an engineered mussel protein that has a catechol-like moiety. By way of example, the monomer of the engineered mussel protein includes catechol methacrylate. Unlike some conventional orthodontic sealants, the catechol-like moiety forms adhesion networks through hydrogen bonding and metal-ligand complexes with hydroxyapatite without one or more of cleaning, etching, or drying preparation steps. Additionally, the catechol-like moieties may undergo Michael addition with collagen in enamel or in dentin to chemically bond the layer 26 to the tooth surface 22.

Although not shown in FIG. 5, by way of example only, the layer 26 may be on the order of about 100 nanometers thick. The layer 26 may be thicker or thinner than 100 nanometers and may depend on application technique and viscosity of the layer 26. The layer 26 may be very thin relative to the overall thickness of the joint formed by the adhesive system 10 between the bracket body 12 and tooth 14. The layers 28, 30, and 32 may be separately applied on the monomer of layer 26 attached to the tooth surface 22.

The layer 28 may be in direct contact and may chemically bond with the catechol-like containing monomer that forms the layer 26 before or after that layer cures. In the embodiment shown in FIG. 5, the layer 28 may include a nitrocatechol and nitrocatechol derivative-containing compound (described below) that bonds to the dried monomer that forms the layer 26. While not being restricted to any particular thickness, in one embodiment, the layer 28 is about 100 nm to about 500 nm. In an exemplary embodiment, the layer 28 denatures when exposed to a specific wavelength of light. Thus, at the end of treatment, the clinician can utilize the light device 100 to expose the system 10 to that light to denature layer 28. As a result, that layer dissolves and releases the orthodontic bracket 12 or remainder of the attachment 10 from the tooth 14. The clinician then easily removes the orthodontic bracket 12 or remainder of the attachment 10. The patient or clinician may remove residual layer 26 with a normal tooth brush.

In one embodiment, and with reference to FIG. 5, a sealant may form layer 30. The layer 30 may be in direct contact and may chemically bond with the nitrocatechol and nitrocatechol derivative-containing compound that forms the layer 28 before or after that layer cures. In the embodiment shown in FIG. 5, the layer 30 may be an acrylate-based resin sealant that bonds to the layer 28. In one embodiment, the sealant forming the layer 30 is a commercially available orthodontic sealant, such as Ortho Solo™, available from Kerr Corporation of Orange, CA.

As shown, the layer 32 may then be directly applied on the layer 30 in a separate application. The layer 32 chemically bonds to the layer 30 and also mechanically bonds to the orthodontic bracket 12. The layer 32 may be preshaped to form the bulk of the attachment 10. By way of example only, the layer 32 may include a resin, such as a methacrylic resin, which may include an acrylate and/or a methacrylate moiety that chemically bonds with the acrylate-based resin sealant of layer 30 when exposed to a preselected wavelength of light. In one embodiment, the light device 100 is also capable of producing the preselected wavelength of light necessary to initiate curing of the adhesive 10 and, in particular, the layer 32. When applied, the layer 32 may include a photo-initiator to facilitate curing of the layer 32. In one embodiment, the resin is a commercially available orthodontic adhesive, such as Grēngloo® or Blūgloo, each of which is commercially available from Ormco Corporation of Orange, CA.

Figure 3B:
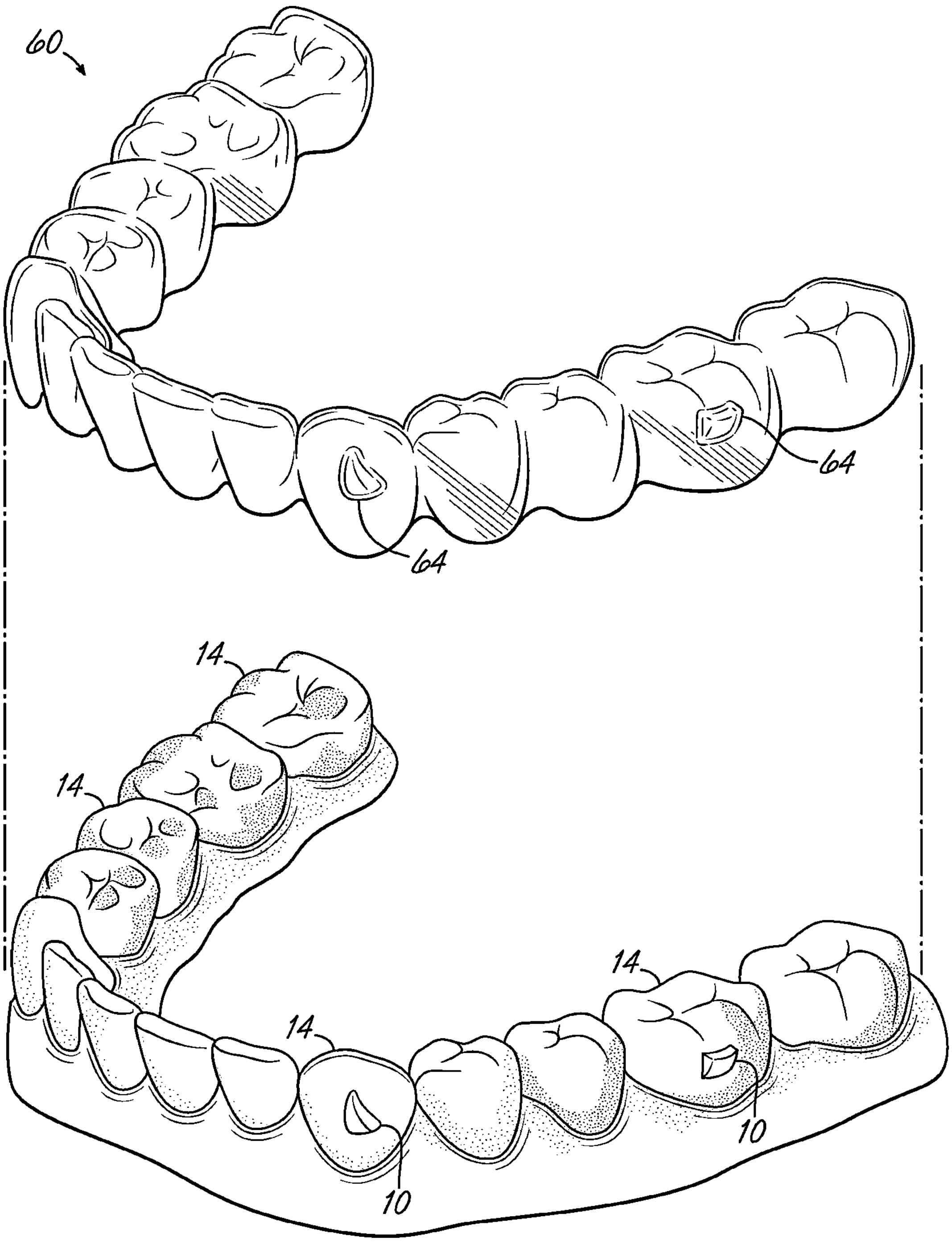
FIG. 3B is a perspective view of attachments for use with an aligner to facilitate orthodontic treatment.
Figure 9A:
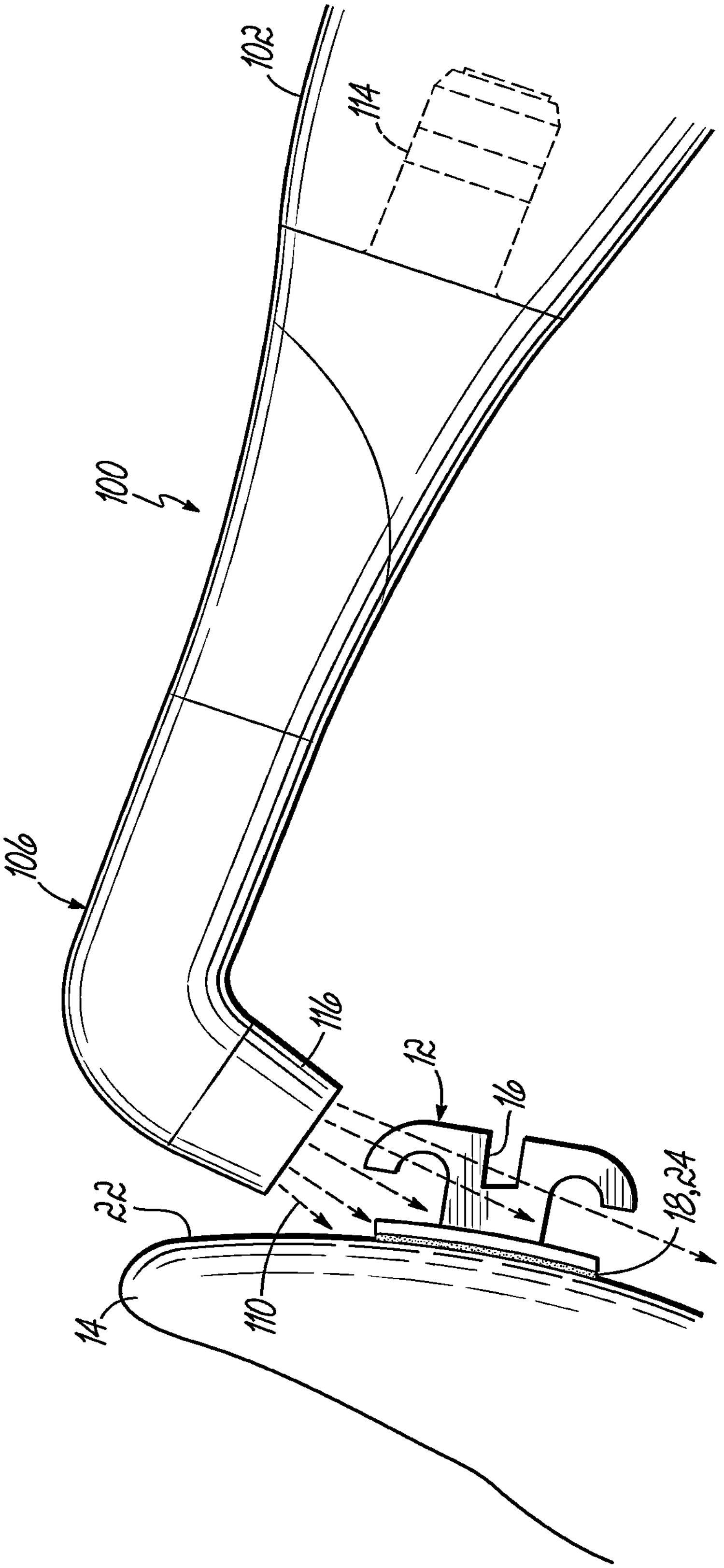
FIG. 9A is a schematic representation of one application of the light device of FIG. 1 for irradiating a bond between an orthodontic bracket and a tooth.

In the case of the layer 32, which may include the photo-initiator, the orthodontic bracket 12 may be pressed against the composite layer 26, 28, 30, and 32 shown in FIG. 5. The adhesive layer 32 may then be cured by activating the light device 100. For example, as is shown in FIG. 9A, the clinician may position the tip structure 106 to irradiate the layers according to 110 with visible blue light (e.g., wavelengths of 450 nm to 495 nm). This photo-curing process cures at least the layer 32. By way of further example, each of the layers 26, 28, 30, and 32 may be cured at the same time or at different times. Although not shown, the timing of each cure depends on the preferences of the clinician. A clinician may prefer to partially cure the layer 26 to make it tackier and then apply the remaining layers with a final cure of each of the layers 26, 28, 30, and 32 together. When the layers 26, 28, 30, and 32 are cured, the orthodontic adhesive system 10 bonds the orthodontic bracket 12 to the tooth surface 22 (FIG. 3A) or forms an attachment 10 (FIG. 3B).

In the exemplary orthodontic adhesive systems 10 shown in FIGS. 5, 6, and 7, the functionalities described above with regard to the layers 26, 28, 30, and 32 may be combined in fewer than four layers. For example, the functionality of layers 28 and 30 may be combined resulting in a three-layer system (FIG. 6). By way of further example, a two-layer system (FIG. 7) may combine the functionality of the catechol-like moiety of layer 26 with a sealant, such as that described above in layer 30, which may include a nitrocatechol and nitrocatechol derivative-containing compound. In this case, the functionality of layers 26, 28, and 30 of FIG. 5 is present in a layer 40 of FIG. 7. Thus, with reference to FIG. 7, the layer 40 is applied to the tooth surface 22. The catechol-like moiety of the layer 40 may form adhesion networks through hydrogen bonding and metal-ligand complexes with the enamel at the surface 22 without one or more of cleaning, etching, or drying.

With reference to FIG. 7, the layer 42 may be similar to the layer 32 of FIG. 5. Specifically, the layer 42 may include a resin, such as a methacrylic resin, which may include an acrylate and/or a methacrylate moiety that chemically bonds with a resin of layer 40. In FIG. 8, the orthodontic adhesive system 10 includes the single layer 18 having components which combine the functions of the layers 26, 28, 30, and 32 described above. By way of example, a catechol-like moiety of the layer 18 may form adhesion networks through hydrogen bonding and metal-ligand complexes with enamel without one or more of cleaning, etching, or drying the tooth surface 22. And, the layer 18 may include a debonding compound and a resin, such as a methacrylic resin, which may include an acrylate and/or a methacrylate moiety that chemically bonds with the acrylate-based resin sealant and forms a bond between the orthodontic adhesive system 10 and the bracket 12. The figures are not drawn to scale. Thus, while layers 26, 28, 30, and 32 in FIG. 5; layers 26, 30, and 32 in FIG. 6; layers 40 and 42 in FIG. 7; and layer 18 in FIG. 8, are depicted as being uniformly thick in approximately equal thicknesses, the layers are not limited to the relative ratios of the thicknesses shown. The thickness of each layer can vary independently of the other layers.

By way of example, the photocleavable moiety of the orthodontic adhesive system 10 may be any moiety that is capable of being broken when exposed to light in at least one of the IR spectrum (i.e., wavelengths of about 700 nm to about 1 mm), NIR spectrum (i.e., wavelengths of about 780 nm to about 2500 nm), light in the UV spectrum (i.e., wavelengths of about 10 nm to about 400 nm), or a combination of IR/NIR and UV spectrum. Photocleavable moiety may include photocleavable bis-methacrylate. The bis-methacrylate chain length may be modified to optimize the debonding parameters. For example, lengthening the polymer chain may reduce the time for debonding. Exposure to, for example, IR light may depolymerize the orthodontic adhesive system 10 and so aid in the debonding of the bracket 12 from the tooth surface 22. It is believed that IR light is advantageous because it passes through both hard (e.g., tooth) and soft (e.g., lips, cheek, and tongue) tissues. The clinician may more easily expose the orthodontic adhesive system 10 to IR light to debond brackets 12 from the teeth 14. Alternatively, the photocleavable moiety may be broken when exposed only to light in the UV spectrum.

Once treatment is complete, in one embodiment, the clinician utilizes the light device 100 to debond the orthodontic brackets 12 by activating the light device 100 and exposing the adhesive to light in the IR spectrum from the light device 100. Alternatively, the light device 100 may produce light in the UV spectrum. The orthodontic bracket(s) 12 may fall off or only require a slight application of force for removal following exposure to the light. It is thought that any force application in combination with light exposure would be substantially less than conventional forces required to debond orthodontic devices from teeth. In addition to reducing the bonding forces, debonding may minimize or completely eliminate the need for grinding away residual adhesive once the orthodontic device is removed. In cases where conventional adhesives needed to be removed mechanically (i.e., be ground off), patient discomfort from mechanical removal is eliminated using the adhesives in combination with the light devices described herein. Also, emergency appointments may be minimized because the adhesives described herein tend to provide higher adhesion strength. For example, bond strength may reach about 15 MPa or more such that accidental debonding may be minimized. These bond strengths may be achieved while also reducing the time it takes to intentionally debond the orthodontic device.

As applied to the embodiment of FIG. 5, for example, when exposed to IR light or UV light, the layer 28 may denature, in which case the layer 28 may break down so that the bracket 12 and the layers 30 and 32 may be released from the tooth 14. Following debonding, the layer 26 may remain on the tooth surface 22. However, the patient may remove layer 26 by brushing their teeth with toothpaste and a toothbrush. Thus, during treatment, a dental bracket may be strongly adhered to the teeth of a patient when desired, but then may also be easily removed from the teeth when treatment is completed or when the device needs repositioning or replacement, by exposing the adhesive to IR/UV light from the light device 100.

Figure 9B:
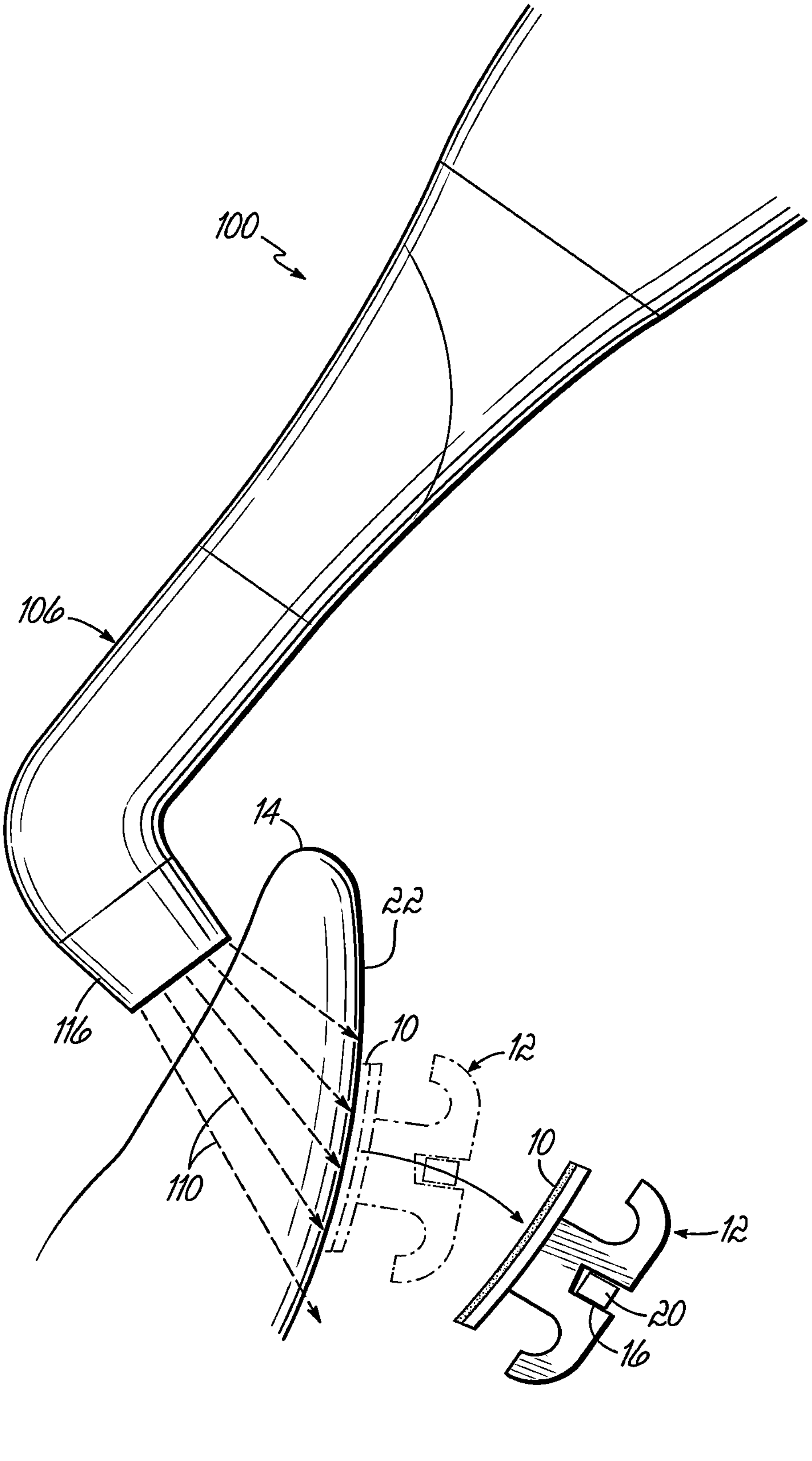
FIG. 9B is a schematic representation of one application of the light device of FIG. 1 for irradiating a bond between an orthodontic bracket and a tooth.

With regard to debonding the orthodontic bracket 12 from the tooth 14, as is illustrated in FIG. 9B, the light device 100 may be positioned to irradiate an adhesive bond between the orthodontic bracket 12 and the tooth 14. The light device 100 produces one or more wavelengths or ranges of wavelengths of light that interact with a photocleavable moiety in the adhesive 10. By way of example only, and not limitation, wavelengths in the UV spectrum or in the IR spectrum or a combination of UV and IR spectrums may react with the adhesive 10 to reduce its bond strength. Not being bound by theory, this reaction may be by a photocleaving process between the light and a component in one or more of the layers 18, 26, 28, 30, 32, 40, and 42 described above and shown in FIGS. 5-8. In one embodiment, photocleaving occurs between the layer 26 and the layer 28 or photocleaving may occur in the layer 28 shown in FIG. 5. The clinician may utilize a similar procedure for debonding the attachment 10 of FIG. 3B from selected teeth 14.

Depending upon the wavelength utilized during debonding and the location of the orthodontic appliance, the clinician may position the tip structure 106 lingually of the tooth 14. For a lingually located appliance, the tip structure 106 may be positioned to directly irradiate the appliance and/or the attachment. Alternatively, the tip structure may be positioned so that radiation from the light device 100 passes through the tooth 14. It will be appreciated that human teeth are transparent or translucent to certain wavelengths of light so that debonding by irradiating the adhesive 10 through the tooth 14 is only appropriate for those wavelengths. One advantage of irradiating the adhesive 10 through the tooth 14 is that it may uniformly expose the adhesive bond to the light from the tip structure 106. That is, the entire interface between the tooth and the bond may be uniformly irradiated and so increase the probability that the adhesive is uniformly weakened. This may produce a uniform release of the bracket 12 or attachment 10 from the tooth 14.

Figure 10A:
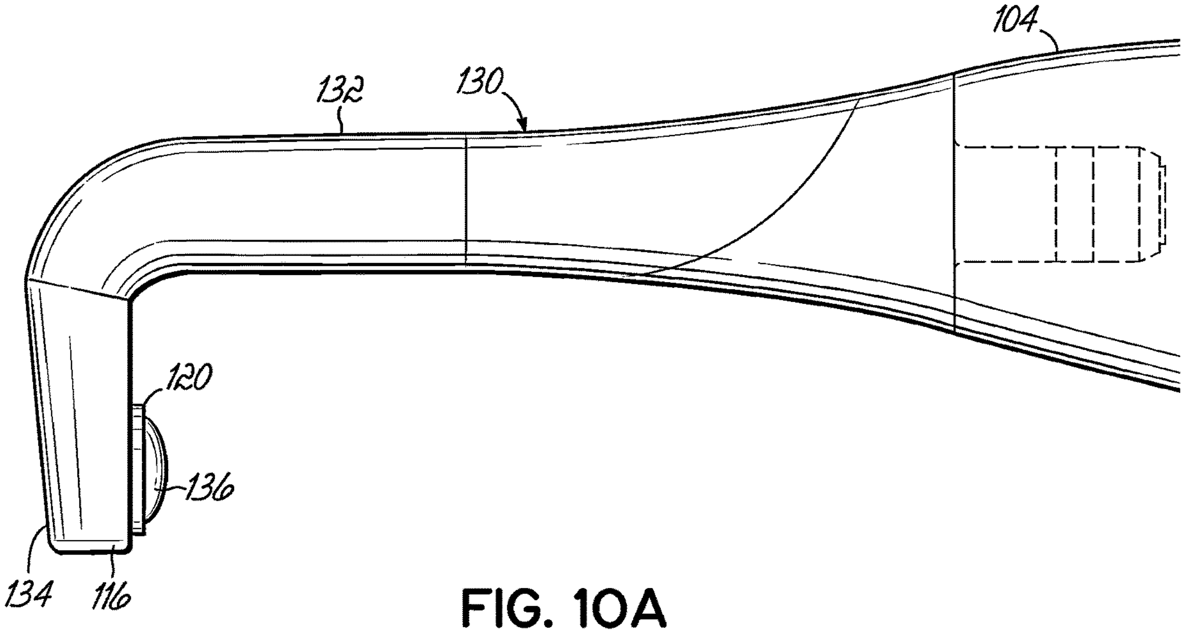
FIG. 10A is an elevation view of a light device according to one embodiment of the invention.
Figure 10B:
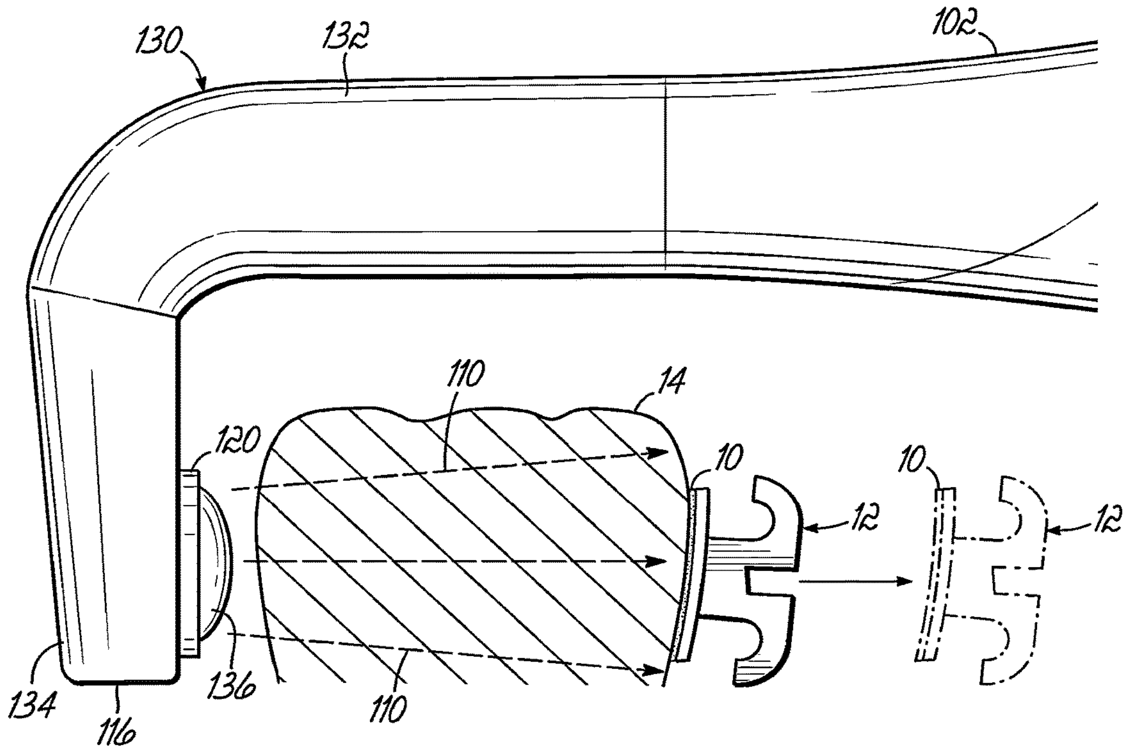
FIG. 10B is a schematic representation of one application of the light device of FIG. 10A shown irradiating a bond between an orthodontic bracket and a tooth.

For debonding applications in which the light device 100 is positioned lingually of the tooth, an alternative tip structure is shown in FIGS. 10A and 10B. A tip structure 130 may be coupled to the handle 104 in a manner similar to the tip structure 106 shown in FIGS. 1 and 2. In one aspect of the light device 100, the tip structures 106, 130 may be interchangeable. With reference to FIG. 10A, the tip structure 130 may have an L-shape in which a first leg 132 extends from the handle 104 and a second leg 134 is generally perpendicular to the first leg 132. As is shown in FIG. 10B, the L-shaped configuration permits more convenient placement of the leg 134 lingually of a tooth 14, such as lingually of a molar 14 shown in FIG. 10B. Light 110 emitted from the light source 120 may be directed from the tip structure 130 through the tooth 14 to irradiate the bond between the orthodontic bracket 12 and the tooth 14. As is described above, the bracket 12 may then fall off the tooth 14 or be gently mechanically removed, such as with the device shown in FIGS. 15A and 15B (described below), a pair of pliers, tweezers, or with fingers.

For wavelengths that will not fully penetrate through the tooth 14, the tip structure 106 may be positioned similar to that shown in FIG. 9A. The clinician may move the tip structure 106 relative to the bracket 12 to more uniformly irradiate the adhesive 10 in this orientation. Once the adhesive 10 is sufficiently weakened, the bracket 12 may be forcibly removed from the tooth 14 or the bracket 12 may fall off the tooth 14, as is shown in FIG. 9B. Thus, the light device 100 in combination with the adhesive system 10 disclosed herein may provide a noncontact technique for removal of orthodontic appliances from teeth at the end of treatment and/or during treatment so that the bracket 12 may be repositioned or a different bracket may be attached to the tooth 14. The light devices described herein may offer a pain free method of removing orthodontic appliances. No physical contact between a tool and the orthodontic appliance may be required to remove the appliance. In that case, the actinic radiation may be sufficient to separate the orthodontic appliance from the tooth. Patients no longer need to fear removal following or during orthodontic treatment.

In addition, one or more of the layers 18, 26, 28, 30, 32, 40, and 42 may remain attached to the bracket 12 during removal. This is schematically shown in FIGS. 9B and 10B where the removed orthodontic bracket 12 includes adhesive 10. Advantageously, little or no adhesive residue may remain on the tooth 14. In those cases, the clinician dispenses with any post-debonding cleanup of the tooth surface. For example, the clinician may not have to grind away residual adhesive following debonding. By way of example, a typical orthodontic bracket may be bonded to the tooth and achieve a shear strength of from 10 MPa to 20 MPa. IR or UV light exposure may reduce that shear strength to 1 MPa or less. Bond strength may be reduced to less than 20% of the bond strength observed during orthodontic treatment. Shearing the adhesive with application of light shear forces may occur at or near the tooth surface so that post debonding cleanup is mostly avoided.

The light device 100 with tip structure 106 or 130 shown in FIGS. 1, 9A, 9B, 10A, or 10B may be focused on a single tooth and so may be utilized to provide treatment to an adhesive bond between one tooth and one orthodontic appliance. This treatment may be achieved on a one-at-a-time basis and may be beneficial in situations where the clinician may need to debond a single bracket from a tooth so that the bracket may be re-bonded to the tooth in a different location or perhaps the bracket design may be changed on that particular tooth. Additional adhesive bonds may be treated by directing the light 110 from the tip structure 106, 130 to other bonds on a bond-by-bond basis. However, other tip structures may be utilized to irradiate multiple teeth or the patient's entire jaw in a single exposure.

In that regard, and with reference to FIGS. 11-14, 17A-18, and 20A-20B various tip structures are disclosed which may be utilized with the handle 104 shown in FIG. 1 and so may be used interchangeably with the tip structures 106 and 130, described above. In general, the devices and tip structures described herein address the needs of the clinician from a comfort standpoint. That is, while the patient's comfort is of utmost concern, the ergonomics of the clinician are also a consideration. Devices described herein reduce or eliminate discomfort for the clinician. Thus, the clinician is less likely to fatigue and is more likely to repeatedly utilize the device without need for a break. To that end, the devices described herein are designed to access difficult areas of a patient's mouth, including between a cheek and a labial surface of the teeth. The devices locate the light sources to irradiate adhesive without requiring the clinician to hold the device at an uncomfortable angle or the patient may hold the device. In either case, the device may eliminate poor ergonomics for the clinician.

Figure 11:
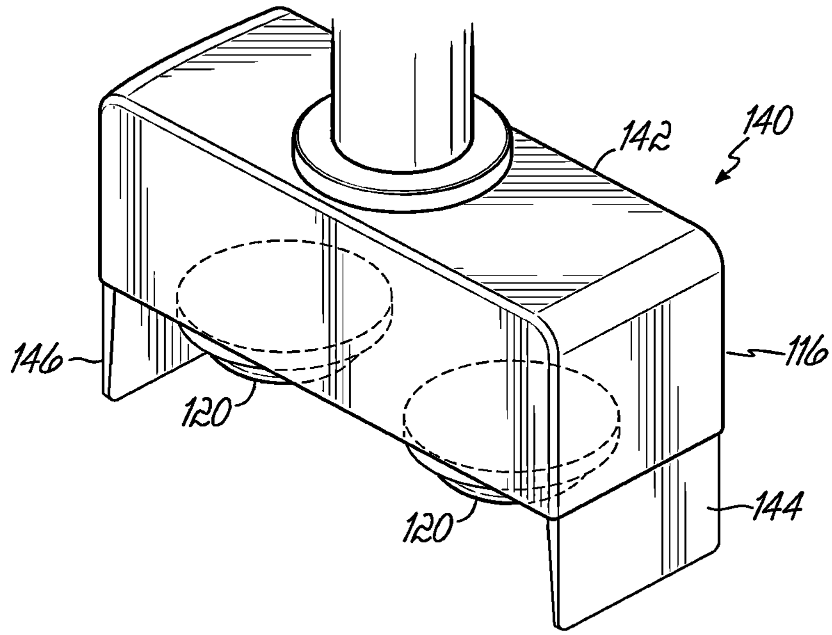
FIG. 11 is a perspective view of a tip portion for use with the light device of FIG. 1.
Figure 12:
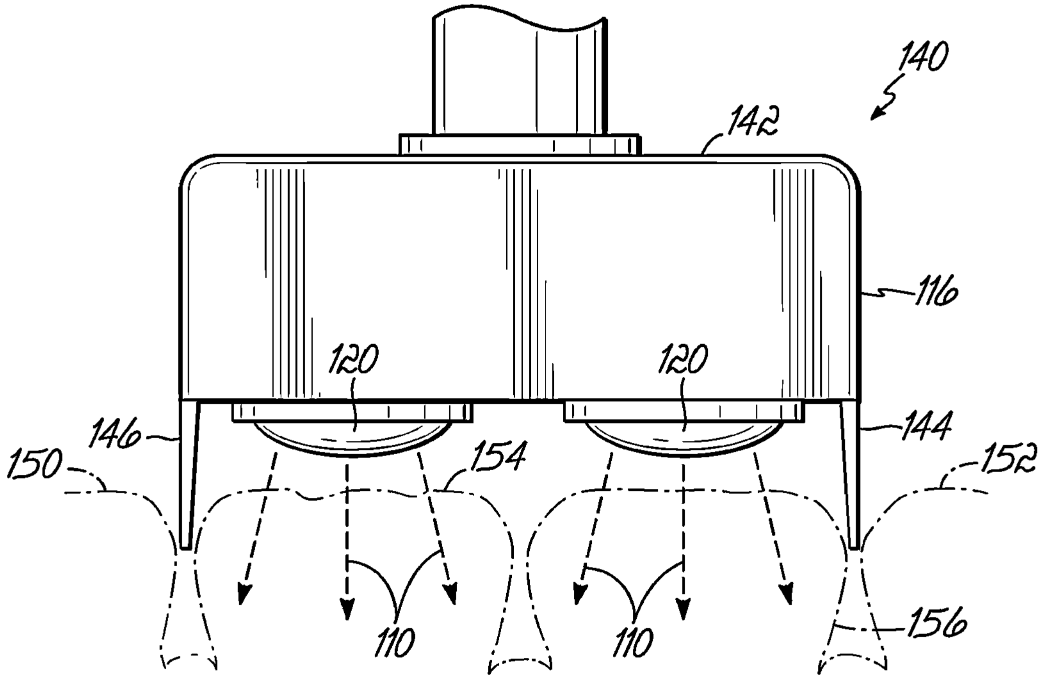
FIG. 12 is a schematic representation of one application of the tip portion shown in FIG. 11 for irradiating a preselected number of teeth according to one embodiment of the invention.

With reference to FIGS. 11 and 12, a tip structure 140 is shown and is capable of irradiating multiple teeth (and adhesive bonds) simultaneously. In the exemplary embodiment shown, the distal end 116 of the tip structure 140 includes a housing 142 within which a plurality of light sources 120 or lenses 136 are located. While two light sources 120 are shown, it will be appreciated that the housing 142 may include three or more light sources or lenses. Further, the number of light sources 120 or lenses 136 may be equivalent to the number of orthodontic appliances and/or teeth being irradiated. Embodiments of the invention are not limited to any relationship, such as a one-to-one relationship, between the number of teeth and the number of light sources 120 or lenses 136.

As shown, the housing 142 includes shields 144 and 146 that generally extend distally past the light sources 120 or lenses 136. When the clinician positions the tip structure 140, the shields 144 and 146 may be positioned between the tooth 150 on the one side and 152 on the opposing side, respectively. In this exemplary embodiment, two teeth 154 and 156 are selected for exposure and are isolated from the teeth 150 and 152. When the light device 100 is activated, light may be prevented from directly impinging upon each of the teeth 150 and 152. The shields 144, 146 may enable the clinician to selectively debond an appliance or attachment from one or both of the teeth 154 and 156 while reducing the radiant energy impinging on adjacent orthodontic appliances and attachments, such as on teeth 150 and 152, and their associated adhesive bonds. Advantageously, the tip structure 140 may allow the clinician to selectively debond while avoiding degradation of adjacent adhesive bonds.

Figure 13:
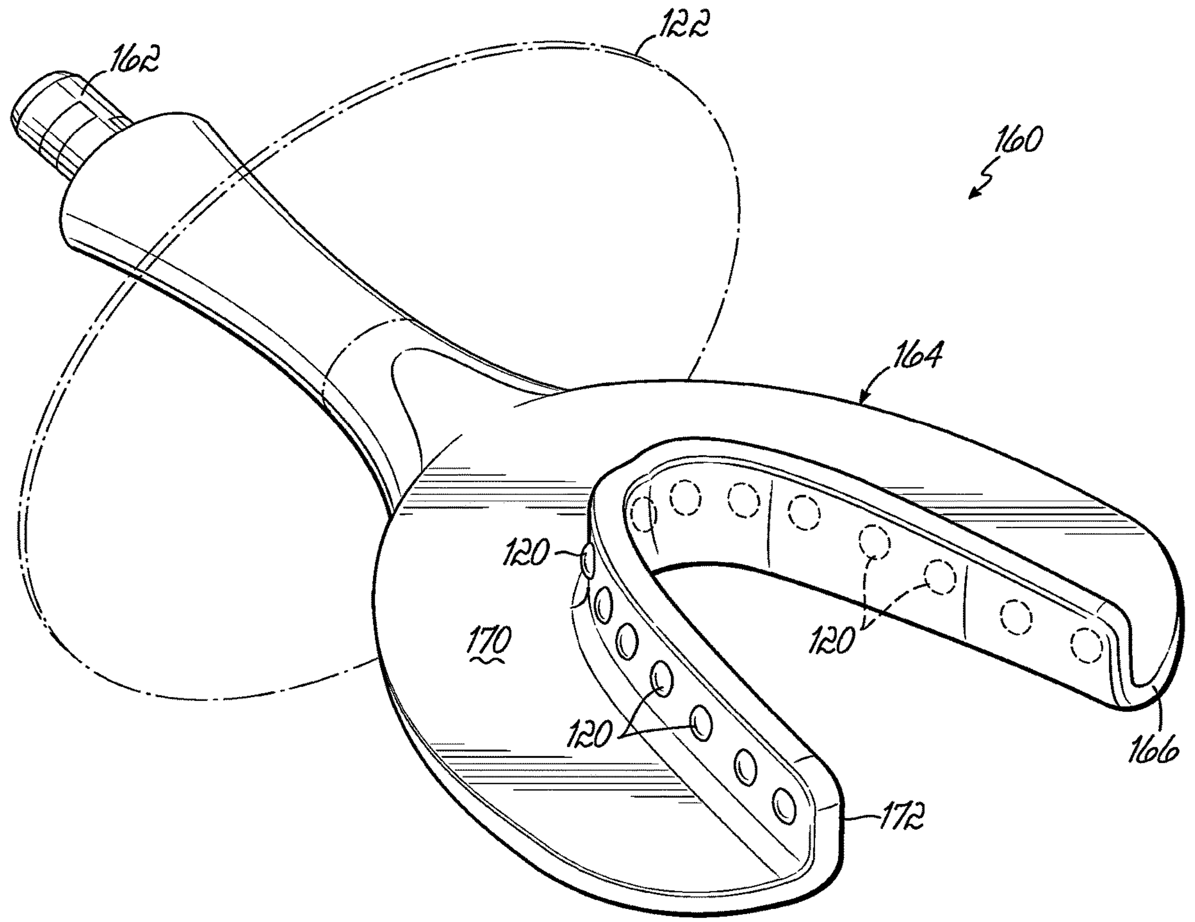
FIG. 13 is a perspective view of a light device according to one embodiment of the invention for irradiating an entire jaw.
Figure 14:
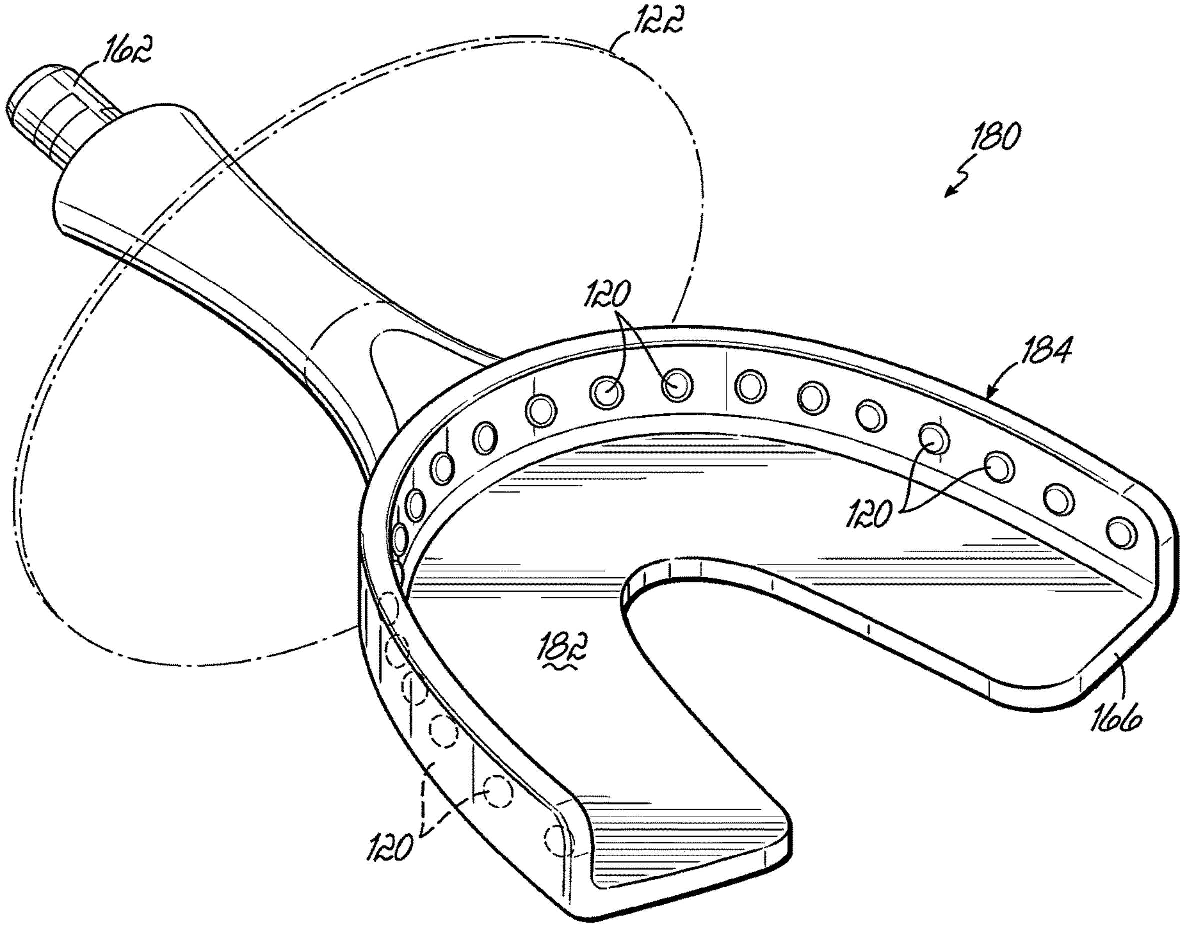
FIG. 14 is a perspective view of the light device according to one embodiment of the invention for irradiating an entire jaw.

With reference to FIGS. 13 and 14, other embodiments of a tip structure are shown. These tips reduce fatigue by placing the light source directly adjacent each of the orthodontic appliances. As shown, the tip structures include light sources to irradiate an entire jaw simultaneously and so eliminate removal of one appliance at a time. Generally, each of the tip structures shown may be utilized at the end of treatment when all the orthodontic appliances on one of the patient's jaws are to be removed from the patient's teeth. That is, the tip structures are configured to irradiate each of the adhesive bonds between an orthodontic bracket and a corresponding one of the patient's teeth. The clinician or the patient may remove multiple brackets 12, even an entire arch of brackets 12, with a single exposure to wavelengths of a selected light spectrum.

To that end, and with reference to FIG. 13, a tip structure 160 may be configured to be removably coupled to the handle 104 (shown in FIG. 1) at a proximal end 162 similar to the proximal end 114 of the tip structure 106 (shown in FIG. 2). The tip structure 160 includes a mouthpiece 164 at a distal end 166. The mouthpiece 164 may be generally shaped according to a human jaw and has a bite plate 170 that is configured to go between the patient's upper and lower jaws and a sidewall 172 that is generally perpendicular to the bite plate 170. When the patient bites on the bite plate 170, the tip structure 160 and handle 104 are held in position without clinician assistance. The sidewall 172 includes multiple light sources 120 (or lenses 136 if the light source is remote from the sidewall 172).

As can be appreciated by FIG. 13, when the tip structure 160 is inserted into the patient's mouth, the sidewall 172 faces the lingual surfaces of all the patient's teeth. When activated, the light sources 120 irradiate attachments or the adhesive between each of the appliances and the corresponding teeth. After a predetermined time, the attachments/appliances may simply fall off the patient's teeth and be captured on the bite plate 170 (e.g., when appliances are bonded to the patient's maxillary jaw). The tip structure 160 is an example of indirect debonding in which the tip structure 160 does not directly contact the appliance. Indirect debonding is in contrast to direct debonding, which is described below with reference to FIGS. 16A and 16B.

Alternatively, in one embodiment of the invention, the clinician may remove multiple brackets 12, even an entire arch of brackets 12, simultaneously by use of the archwire 20. The clinician may expose the orthodontic adhesive system 10 to IR light or UV light, such as with the tip structure 160. Once at least a portion of the orthodontic adhesive system 10 denatures, the clinician may then pull on the archwire 20 while it is still engaged with each bracket 12 on the arch (as shown in FIG. 3A). The brackets 12 detach while still coupled to the archwire 20. In this way, the clinician may remove each of the brackets 12 with one pull on the archwire 20 in combination with use of the tip structure 160. This process may leave no residual adhesive on the teeth 14. As another advantage, this prevents unforeseen loss or ingestion of the individual brackets and can significantly reduce chair time, for example, by greater than 90%.

Further in that regard, and with reference to FIG. 14, a tip structure 180 as shown. The tip structure 180 includes the proximal end 162 so that it may be removably coupled to the handle 104 similarly to the other tip structures described herein. In contrast with the tip structure 160 shown in FIG. 13, the tip structure 180 is configured to emit radiation toward the labial surfaces of the patient's teeth. In that regard, the distal end 166 of the tip structure 180 includes a bite plate 182 in the shape of a human jaw. The bite plate 182 may fit between the patient's upper and lower jaws. Similar to the tip structure 160, when the patient bites down on the bite plate 182, the tip structure 180 remains in position without the clinician's assistance. A sidewall 184 may extend generally perpendicular to the bite plate 182 and include a plurality of light sources 120 (or lenses 136 for a light source remote from the distal end 166 of the tip structure 180). As can be appreciated by FIG. 14, when the tip structure 180 is inserted into the patient's mouth, the sidewall 184 faces the labial surfaces of all the patient's teeth. When activated, the light sources 120 irradiate the adhesive between each of the appliances and the corresponding teeth. After a predetermined time, the appliances may simply fall off the patient's teeth and be captured on the bite plate 182 (e.g., when appliances are bonded to the patient's maxillary jaw).

Although not shown, as an alternative to the embodiments disclosed in the figures, in one embodiment, the tip structure includes a mat in which LEDs and/or a vibrational source are embedded. The mat may be rectangular or U-shaped. The tip structure lays or rests on the teeth. The mat is flexible and conforms to the teeth and orthodontic appliance upon urging of the practitioner or patient or under the influence of gravity. In this way, the mat forms a shell. Activation of the tip structure applies light and/or vibrational energy to the appliance and corresponding bond so that the mat produces a similar result as either tip structures 160, 180.

Figure 15A:
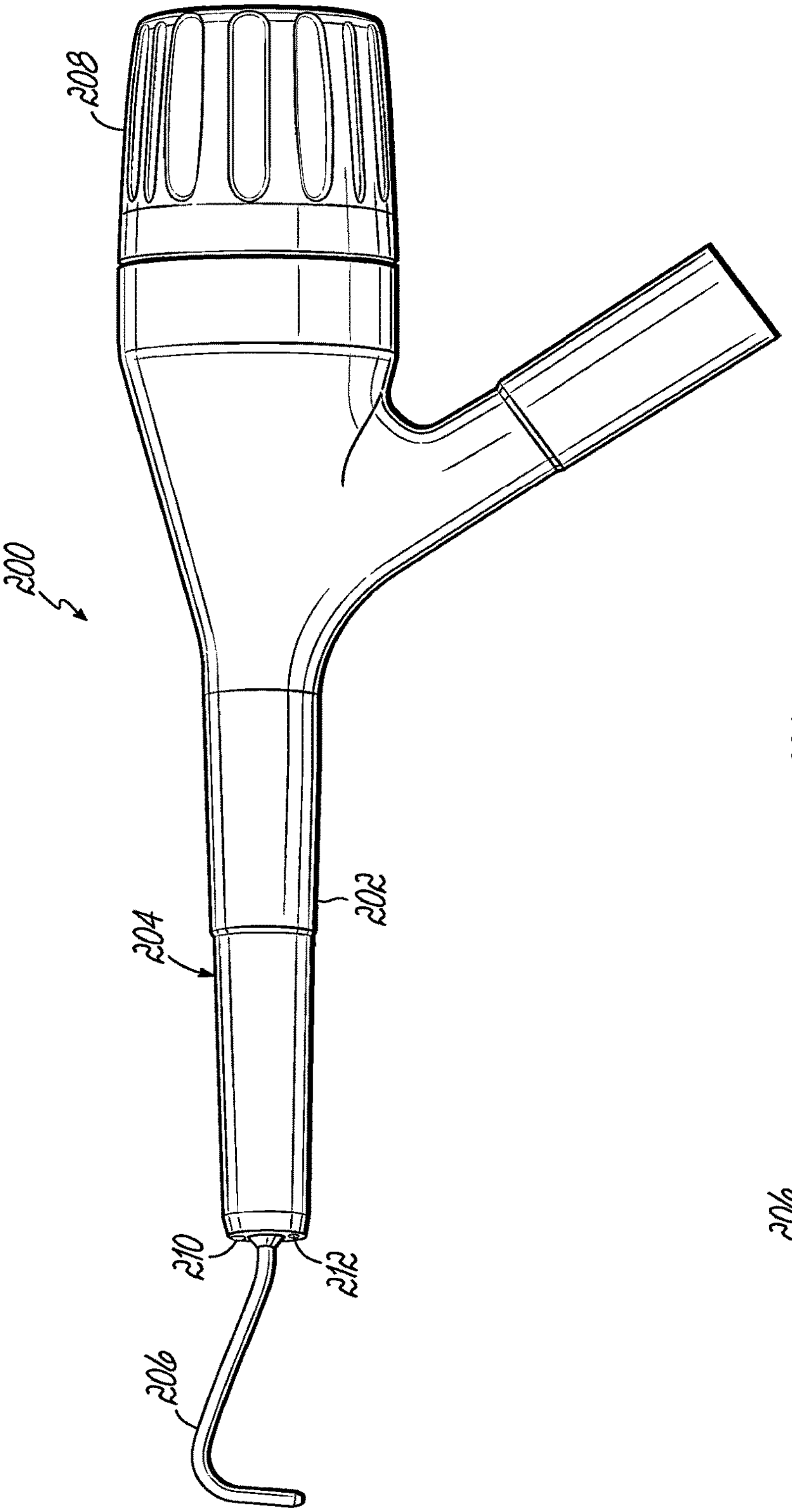
FIG. 15A is an elevation view of a light device according to one embodiment of the invention.
Figure 15B:
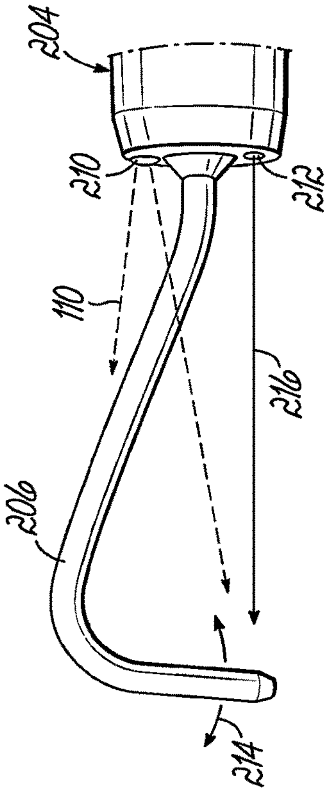
FIG. 15B is an enlarged view of a tip structure of the light device shown in FIG. 15A.

With reference now to FIGS. 15A and 15B, an exemplary light device 200 is shown. The light device 200 is similar to the light device 100 shown in FIG. 1 and includes a housing 202 that defines the handle 204. A tip structure 206, which may be in the form of a scaler, extends from one end of the handle 204 and a fluid reservoir 208 is removably coupled to the handle 204 at the opposing end. The clinician may fill the fluid reservoir 208 with water for use as described below. Light may be emitted from the housing 202 via a light source 210, which directs selected wavelengths of a light spectrum (indicated by arrows 110 in FIG. 15B) toward the patient's teeth. The light source 210 may be positioned adjacent the tip structure 206 and direct light toward the tip structure 206. Thus, the light and the tip structure 206 may be used in combination during debonding. The housing 202 may contain a light source, described above, or be a lens through which light may pass. The light source in that case may be within the housing 202 or be supplied from a remote light source that is coupled to the lens. The housing 202 may also contain a sonic or ultrasonic generator (e.g., a piezoelectric device) coupled to the tip structure 206. The clinician may then turn the generator on and off to control vibration of the tip structure 206 (as is indicated by the arrows 214). Scaler vibration may be in the sonic or ultrasonic range and may be measured in kilohertz. For example, the range may be from about 23 kHz to about 32 kHz. The fluid reservoir 208 may be fluidly coupled through the housing 202 to a port 212 adjacent the tip structure 206. The light device 200 is configured to eject fluid from the fluid reservoir 208 from the port 212 toward the tip structure 206 and thus may impinge upon the patient's teeth. This may be achieved by a pump or other means.

During debonding of an orthodontic appliance, such as debonding an orthodontic bracket, the clinician may simultaneously expose the adhesive to light from the light source 210 according to arrows 110 in FIG. 15B and then contact the tip structure 206 with the orthodontic bracket. The clinician may touch the orthodontic bracket with the tip structure 206 while exposing the adhesive to light 110. The tip structure 206 is an example of direct debonding. The shear forces on the bracket may be sufficient to remove it from the patient's tooth. Alternatively, the clinician may apply additional mechanical energy by activating the vibration source so that the tip structure 206 vibrates against the orthodontic bracket. In that regard, the clinician may selectively spray fluid (according to arrow 216 in FIG. 15B) from the reservoir 208 from the port 212 toward the tooth. Advantageously, the fluid may act to cool the tooth during debonding and so may eliminate the possibility of patient discomfort due to heat in the tooth.

In view of the above, one method to remove an orthodontic bracket from a tooth may be to utilize the light device 200 to apply 5,000 mW of NIR light (about 980 nm or about 940 nm) or UV light (about 395 nm or about 365) (as used herein with respect to wavelength "about" means plus or minus 5 nm) for at least about 5 seconds along with a low-speed vibration to the scaler portion of the tip structure 206. It is believed that a layer, such as layer 28 (shown in FIG. 5), exposed to a combination of light and mechanical vibration will break and so provide a consistent, predictable failure location. Ultimately, the adhesive bond may be reduced from a strength of about 20 MPa to about 1 MPa and the adhesive may be removed from the tooth with little or no residual adhesive on the tooth. As another example, one method of removing an orthodontic bracket includes irradiating an adhesive with light at 940 nm at 2.74 W in combination with ultrasonic vibration in the range of 28 kHz to 32 kHz. This produces a radiant flux of 204 mW. Exposure time is sufficient so that the adhesive receives a dosage of 423.7 J/cm$^2$. The combination of light and vibration is sufficient to remove the orthodontic appliance.

In another exemplary method, an orthodontic bracket may be removed with the light device 200 by application of 10 W of UV light (e.g., at a wavelength of about 395 nm) and by contacting the orthodontic bracket with a low ultrasonic vibration tool. As another example in the UV spectrum, light of a wavelength of 365 nm at 3.08 W in combination with ultrasonic vibration of 28 kHz is sufficient to debond an orthodontic appliance. The combinations of light and vibrational energy may be applied to the orthodontic appliance/adhesive according to any single one of the devices described herein that is capable of irradiating an adhesive and contacting the orthodontic appliance. It will be appreciated that while irradiating and contacting may be simultaneous, embodiments of the invention are not limited to simultaneous application of light and vibration.

Figure 16B:
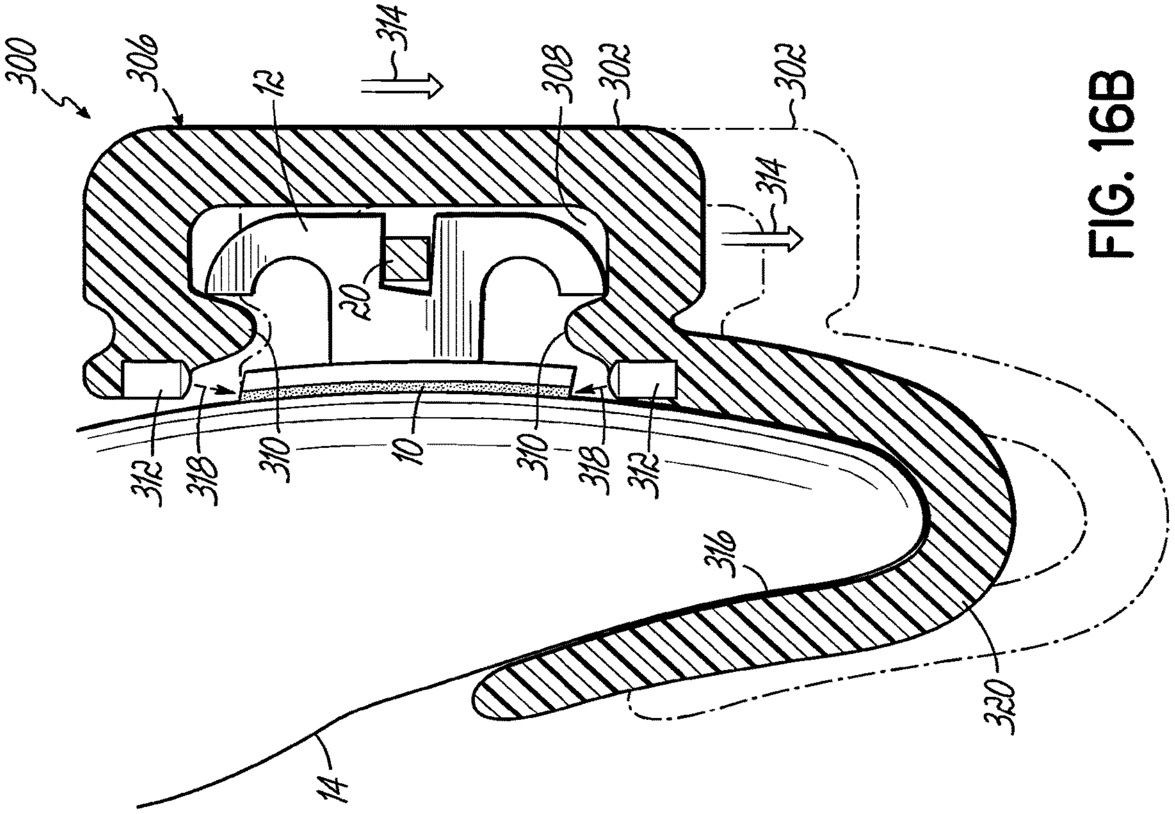
FIGS. 16A-16C are schematic partial cross-sectional views of one embodiment of a light device.
Figure 16A:
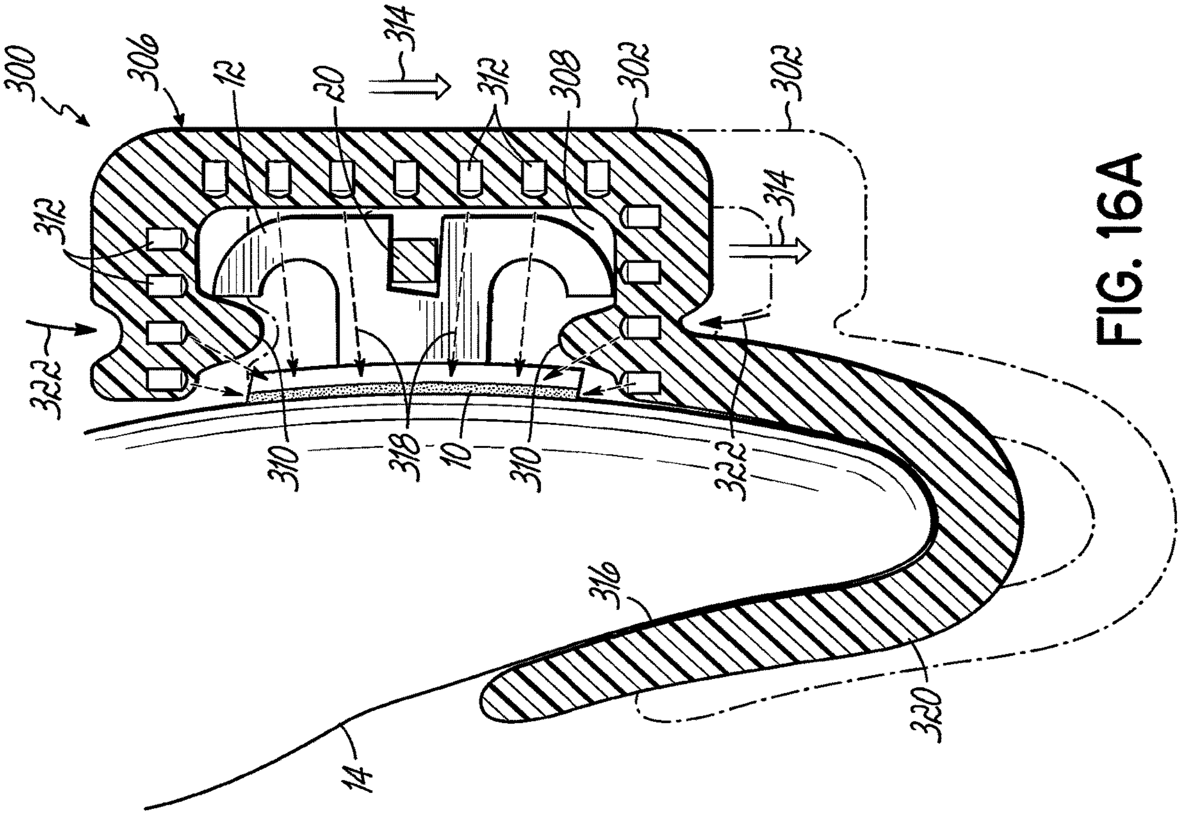

With reference now to FIG. 16A, an exemplary light device 300 is shown and is similar in function to the light device 200 described above. In that regard, the light device 300 physically contacts an orthodontic bracket to permit application of mechanical debonding force to that bracket during or immediately following exposure of an adhesive to light and is another example of direct debonding. In the exemplary embodiment shown in FIG. 16A, the light device 300 has a shell 302 that conforms to the bracket 12 and to the tooth 14. A cavity portion 306 of the shell 302 defines a cavity 308 that encloses the bracket 12 at least in an occlusal direction and in a labial direction. At least one projection 310 may close off a portion of the cavity 308 to produce an interference fit with the bracket 12 in one of the labial direction or the lingual direction. In the exemplary embodiment, the shell 302 includes a pair of opposing projections 310. It will be appreciated that the direction of the interference fit depends upon which surface of the tooth the bracket 12 is bonded to.

The shell 302 may be made of an elastic material, such as polyurethane or similar polymer, and so the clinician may elastically deform the cavity portion 306 so that the projections 310 fit over the bracket 12. By way of example only, the shell 302 may be similar in configuration to an aligner. By deforming the cavity portion 306, the projections 310 essentially pinch the bracket 12 in the cavity 308. This is shown by way of example with regard to the arrows 322 in FIG. 16A. In this way, the light device 300 may removably receive the bracket 12 within the cavity 308.

Embedded within the shell 302 are a plurality of light sources 312, which may be similar to the light sources 120 described above or different light sources. The light sources 312 are arranged in the shell 302 to illuminate the adhesive 10 according to arrows 318. As is shown in FIG. 16A, the light 318 penetrates the bracket 12. It will be appreciated that the bracket 12 in this embodiment may be a ceramic or other material that is transparent or translucent to the light emitted from the light sources 312. The light from the light sources 312 therefore irradiates the adhesive 10 through the bracket 12. Further in that regard, the light sources 312 may be distributed along the entire perimeter of the cavity portion 306 so as to surround the transparent or translucent bracket 12. Although not shown, the light sources 312 may be an array of light sources that is similar in size or larger than the bond area between the adhesive 10 and the bracket 12. This may ensure that the adhesive 10 is uniformly irradiated.

The clinician may then leave the light device 300 on the patient's teeth. That is, the clinician need not hold the light device 300 in any particular orientation relative to the adhesive 10 during irradiation. Activating the light sources 312 reduces the strength of the adhesive 10 as is described above. In one embodiment, the clinician may secure the light device 300 to the patient's teeth, activate the light sources 312 and then proceed to simply wait for a predetermined time. During this period, for example, the clinician may attend to other patients.

Once the adhesive 10 is sufficiently weakened, the clinician may remove the orthodontic bracket 12 from the tooth 14. In one embodiment, the clinician may apply a shear force in the direction of the arrow 314 shown in FIG. 16A on the light device 300 to remove the orthodontic bracket 12 from the tooth 14. The orthodontic bracket 12 is contained within the cavity 308 upon removal of the light device 300 from the tooth 14. Although not shown in FIG. 16A, the light device 300 may span multiple orthodontic brackets as is shown in FIG. 3A. In that instance, the clinician may remove the light device 300 following irradiation of the adhesive 10 between each of the brackets 12 and the corresponding tooth 14 and in doing so remove an entire arch of orthodontic brackets (this may also include removal of the archwire 20) or selected ones of the orthodontic brackets with a single motion in the occlusal direction as is indicated by arrow 314.

In one embodiment, the shell 302 may further include a second cavity 316 that receives at least an occlusal edge of the tooth 14. As shown in FIG. 16A, the shell 302 includes a U-shaped portion 320 that extends from the cavity portion 306. The U-shaped portion 320 defines the second cavity 316 and may be sized specific to the patient's teeth and so provide a friction-type fit. Advantageously, the second cavity 316 may hold the light device 300 in position on the patient's tooth 14 irrespective of orientation of the light device 300 and after the adhesive 10 no longer adheres the orthodontic bracket 12 to the patient's tooth 14. In other words, the second cavity 316 may prevent the device 300 from falling off the patient's teeth in the absence of an adhesive bond between the bracket 12 and the tooth 14. The light device 300 contains the bracket 12 and archwire 20, if present, to prevent them from dropping into the patient's mouth during debonding.

Figure 16C:
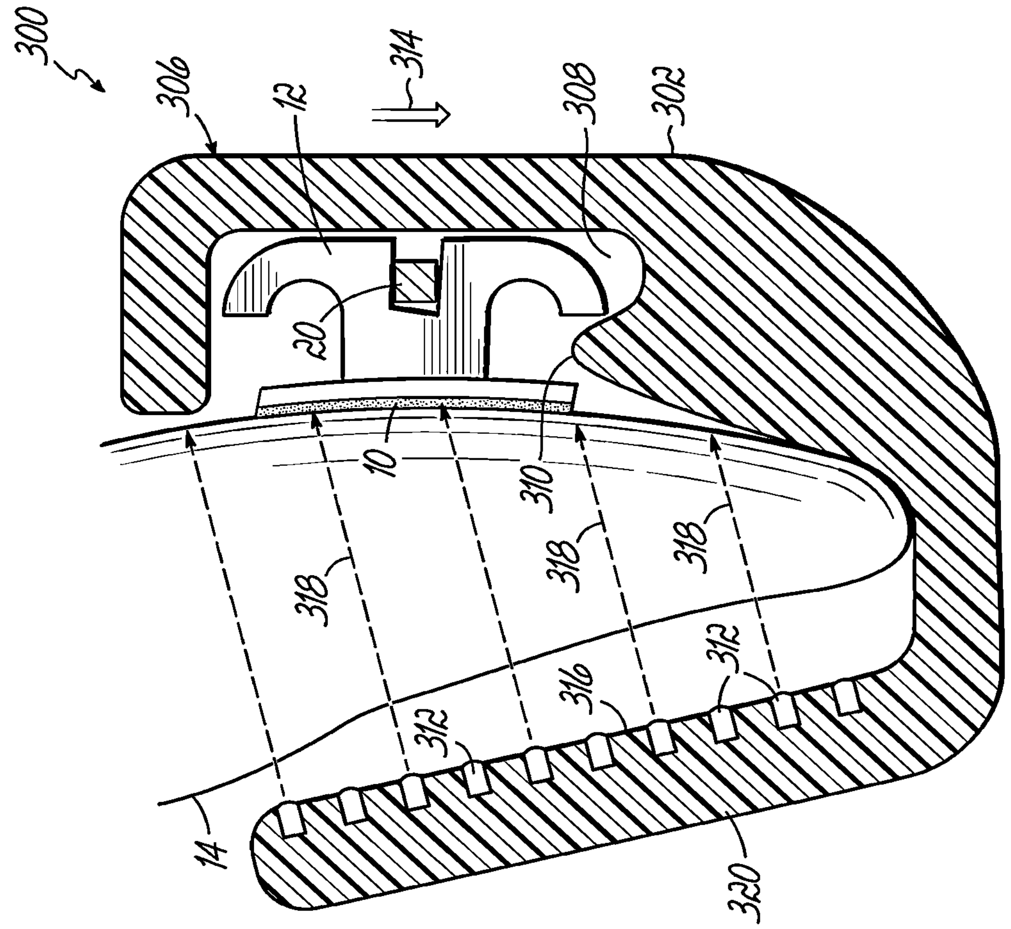

With reference now to FIGS. 16B and 16C in which like reference numerals refer to like features with respect to FIG. 16A, light devices similar to the light device 300 in FIG. 16A are shown. The light device 300 shown in FIG. 16B may be utilized with orthodontic brackets 12 that are not transparent or translucent to light emitted from the light sources. To address non-transparency of metallic brackets, the light sources 312 are placed proximate the projections 310 and so that the light sources 312 are positioned to irradiate an edge portion of the adhesive 10 when activated. Once activated, the light from the light sources 312 deteriorates the strength of the adhesive 10 between the tooth and the bracket 12. After sufficient time, the light device 300 together with the orthodontic bracket 12 may be removed from the patient's tooth 14. By way of example only, removal may include pulling the light device 300 in the direction of the arrow 314.

The light device 300 shown in FIG. 16C may also address the issue of a non-transparent or non-translucent bracket 12. Irradiation of the adhesive 10 may be achieved by positioning the light sources 312 along a portion of the second cavity 316. As shown, the light sources 312 may line the second cavity 316 and be oriented toward the tooth 14. The patient's tooth 14 may be transparent or translucent to selective wavelengths of light, such as wavelengths in the UV spectrum. The light sources 312 may emit light in those wavelengths. The light then penetrates through the patient's tooth to uniformly irradiate the interface between the tooth 14 and the adhesive 10. Once the adhesive 10 is sufficiently weakened, the clinician may remove the orthodontic bracket 12 in accordance with the procedures described in conjunction with FIGS. 16A and 16B.

With reference now to FIGS. 17A-20B, tip structures that physically contact the orthodontic bracket 12 or the archwire 20 so that the clinician may apply tensile debonding forces on the adhesive 10 during or following irradiation with selected wavelengths are shown. Therefore, instead of application of shear force, which is made possible by other light devices described herein, the light devices in FIGS. 17A-20B make it possible for the clinician to pull on the bracket 12 generally perpendicularly to the adhesive 10. Advantageously, this may permit more efficient removal of the bracket 12 and most, if not all, of the adhesive 10 from the tooth 14.

Figure 17B:
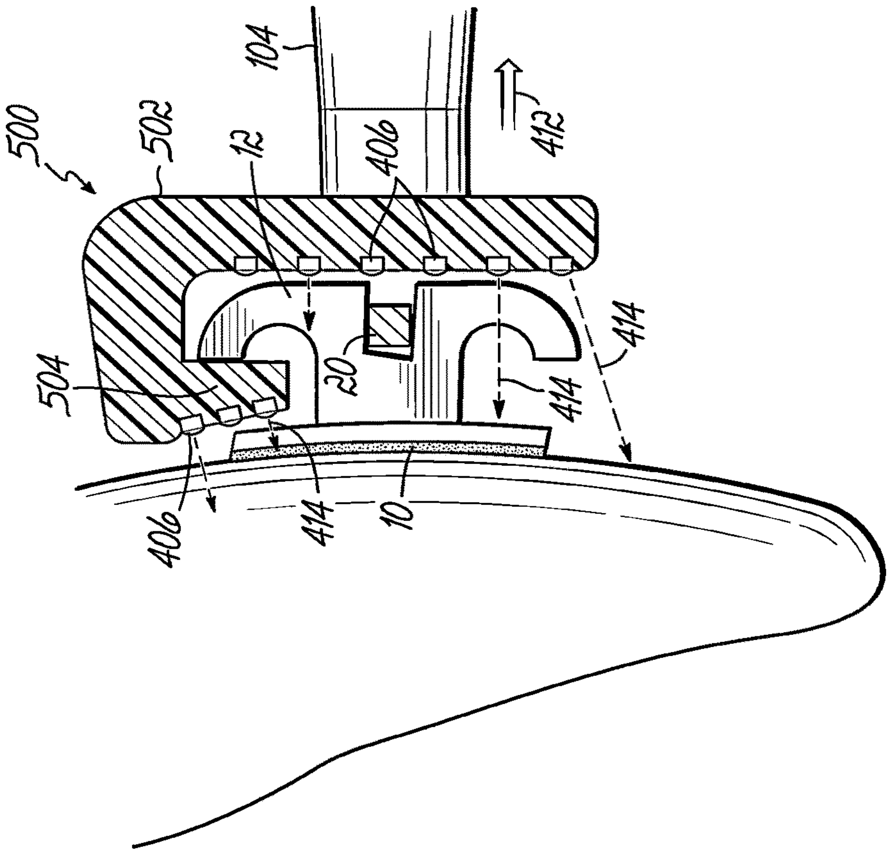
FIGS. 17A-17C are schematic partial cross-sectional views of one embodiment of a light device.
Figure 17A:
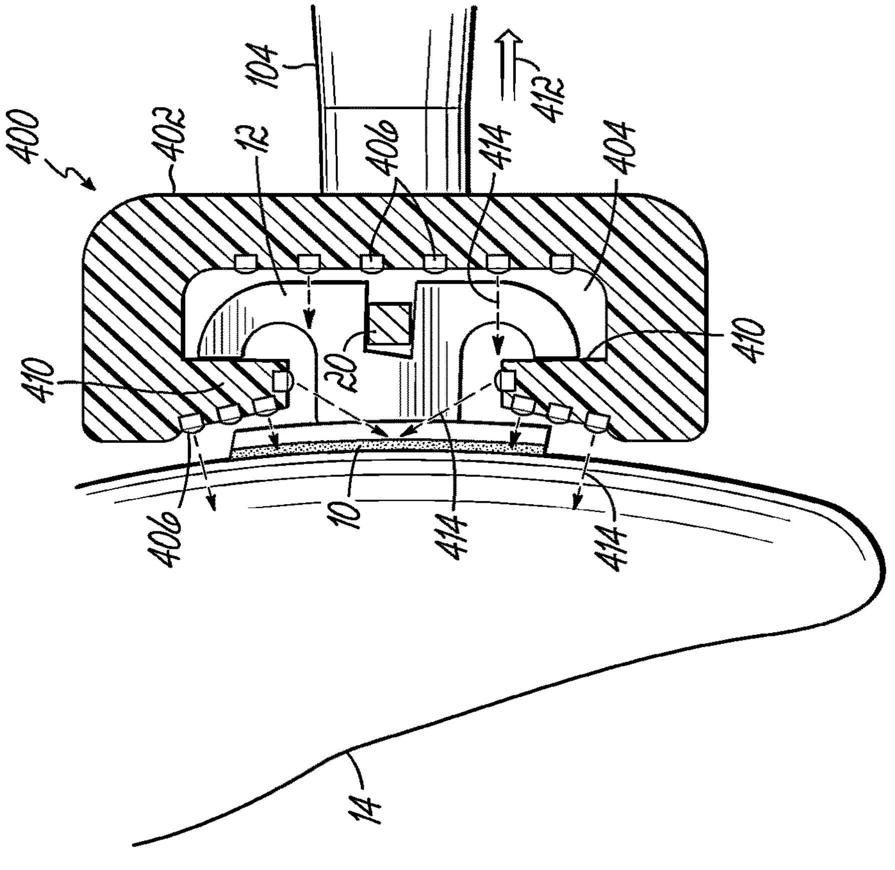
Figure 19:
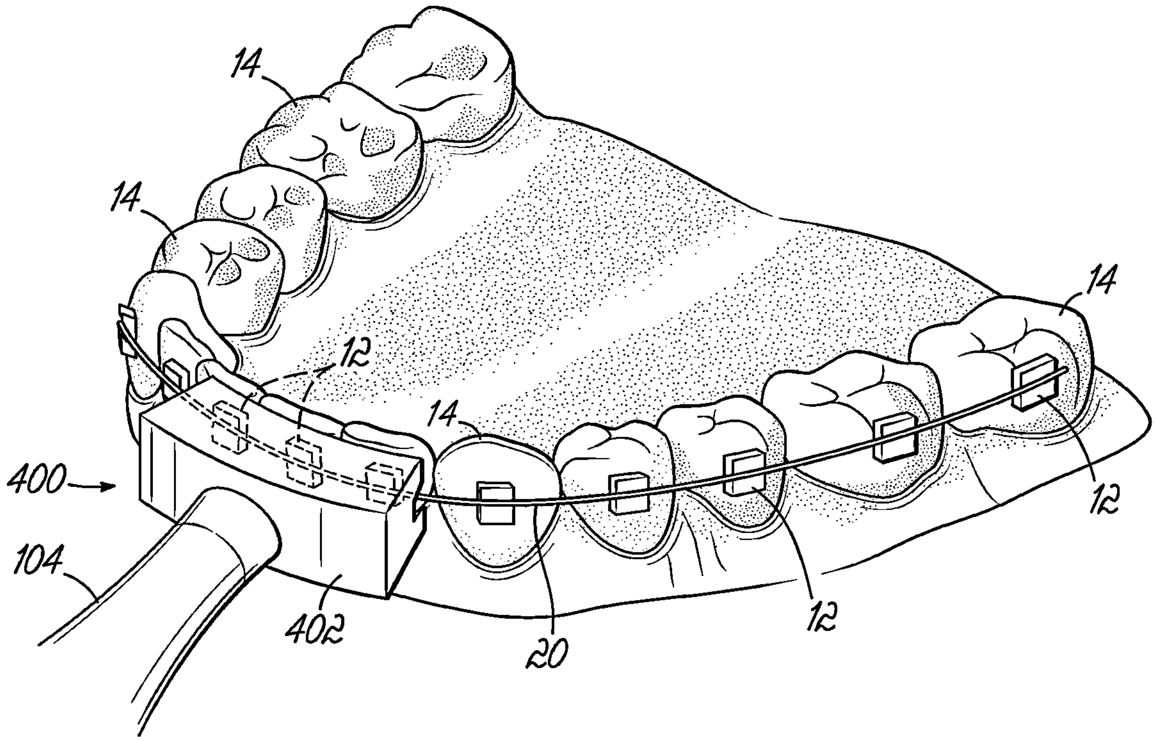
FIG. 19 is a perspective view of one embodiment of a light device.
Figure 20A:
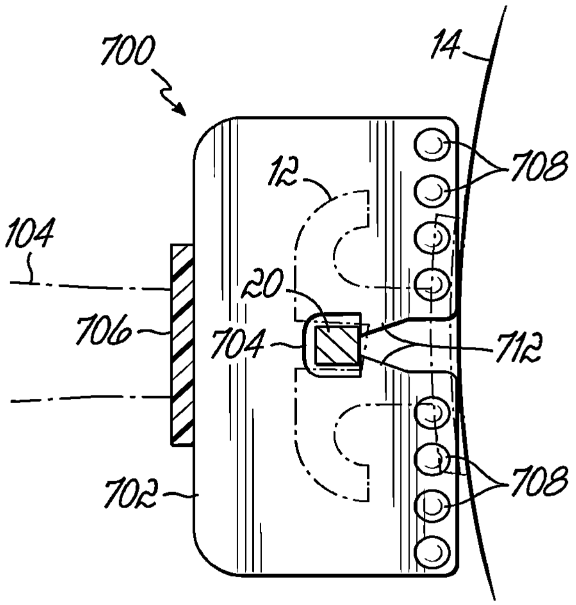
FIG. 20A is an elevational view of one embodiment of a light device.
Figure 20B:
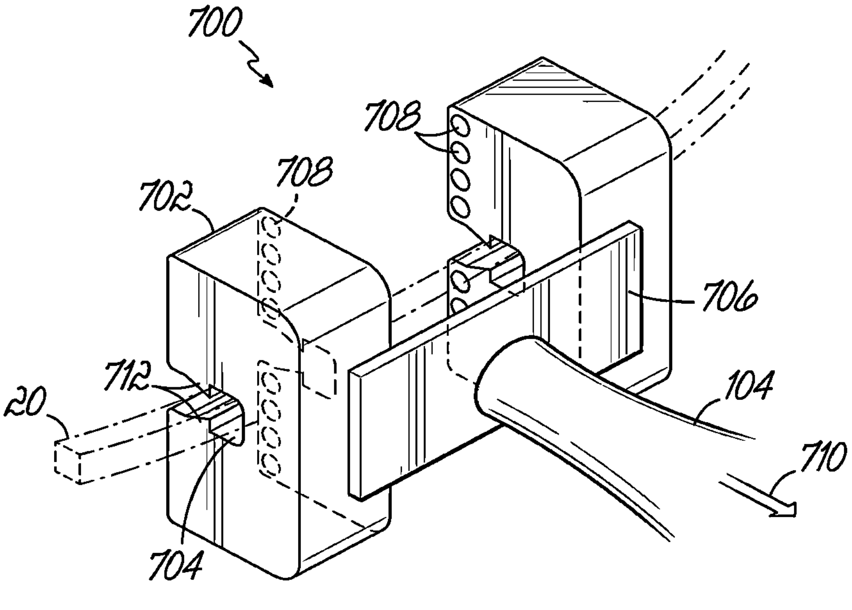
FIG. 20B is a perspective view of one embodiment of a light device.

To that end, for example, and with reference to FIGS. 17A and 19, a tip structure 400 may be removably coupled to a handle, such as the handle 104 shown in FIG. 1. The tip structure 400 may have a configuration similar to the light device 300 shown in FIG. 16A. In that regard, the tip structure 400 is in the form of a shell 402 that defines a cavity 404. The shell 402 surrounds the bracket 12 on at least a labial side, an occlusal side, a gingival side, and a portion of the lingual side, as shown. Although not shown, it will be appreciated that the shell 402 may further surround the mesial and distal sides and so when the orthodontic bracket 12 is inserted into the cavity 404, the tip structure 400 forms an enclosure around the bracket 12. A plurality of light sources 406 may be embedded within the shell 402 and be positioned to irradiate the adhesive 10 from one or more directions. The light sources 406 may be similar to the light sources 120 described above or different light sources.

The shell 402 includes a pair of opposing projections 410 which partially close off the cavity 404 and thereby form an interference fit with the orthodontic bracket 12. Forces applied in the direction of the arrow 412 on the orthodontic bracket 12 place the adhesive 10 in tension. As is shown in the exemplary embodiment, light sources 406 may line a portion of the cavity 404 and each of the projections 410. Activating the light sources 406 may radiate the entirety of the orthodontic bracket 12, and in the case of a transparent or translucent orthodontic bracket 12, the light rays 414 emitted from the light sources 406 may penetrate the orthodontic bracket 12 and so irradiate the adhesive system 10.

Once the adhesive system 10 is sufficiently weakened, the clinician may apply tension to the adhesive system 10 by pulling the tip structure 400 via the handle 104 until the adhesive 10 releases the orthodontic bracket 12. The tip structure 400 may be configured to span multiple orthodontic brackets 12 as is shown in FIG. 19 or even the entire arch of orthodontic brackets. In this way, a single orthodontic bracket 12 may be removed or multiple orthodontic brackets may be removed during a single exposure to light and application of mechanical forces to the weakened bond between each of the selected brackets and the corresponding teeth.

With reference now to FIG. 17B, a tip structure 500 is shown coupled to a handle, such as the handle 104 shown in FIG. 1. The tip structure 500 is similar in many respects to the tip structure 400 shown in FIG. 17A. However, a shell 502 may only surround the orthodontic bracket 12 on a labial side and a gingival side. The occlusal side of the bracket 12 is not enclosed by the shell 502. Consequently, the shell 502 includes a single projection 504. Advantageously, the engagement of the tip structure 500 may be simplified as compared to the tip structure 400 because it is only necessary to engage the projection 504 with the orthodontic bracket 12. This may be achieved by a simple hooking motion whereas it may be necessary to deform the opposing projections 410 of the tip structure 400 to position the bracket 12 in the cavity 404. After exposing the adhesive system 10 to light from the light sources 406, as is generally indicated by arrows 414, the clinician can pull on the bracket 12 in the direction of arrow 412. Pulling engages the projection 504 with the orthodontic bracket 12 to remove the bracket 12 from the patient's tooth 14.

Figure 17C:
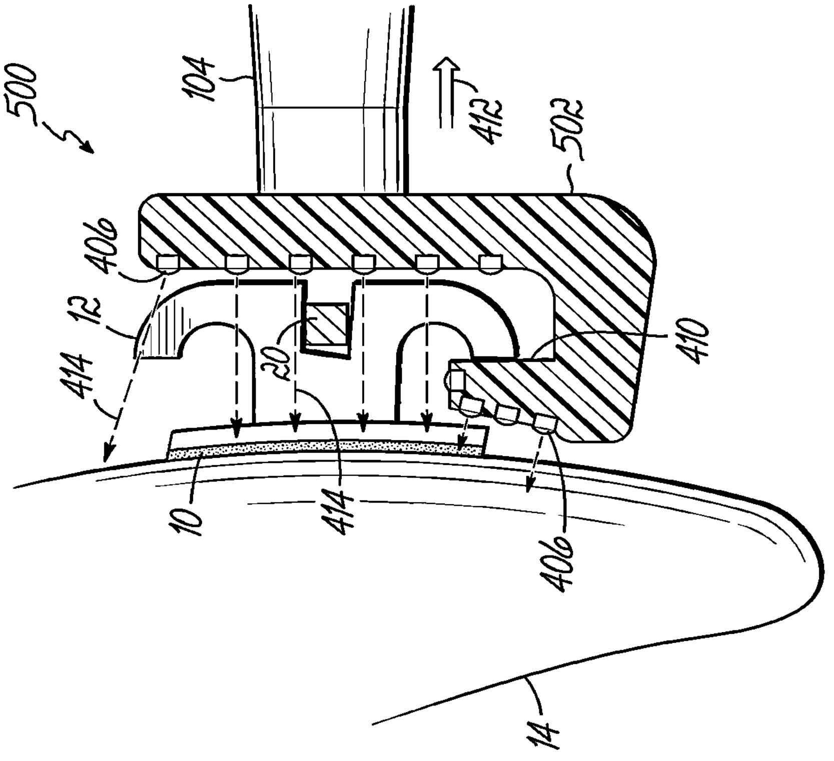

FIG. 17C depicts the tip structure 500 in the reverse orientation from the orientation shown in FIG. 17B. This orientation may be advantageous because once removed, the orthodontic bracket 12 will stay engaged with the tip structure 500 due to gravity. While the tip structure 500 is shown engaged with a single bracket, the tip structure 500 may span multiple brackets, similar to that shown in FIG. 19 with the tip structure 400, and may engage every single one of the brackets along the patient's entire arch. The tip structures described herein may be disposable or autoclavable.

Figure 18:
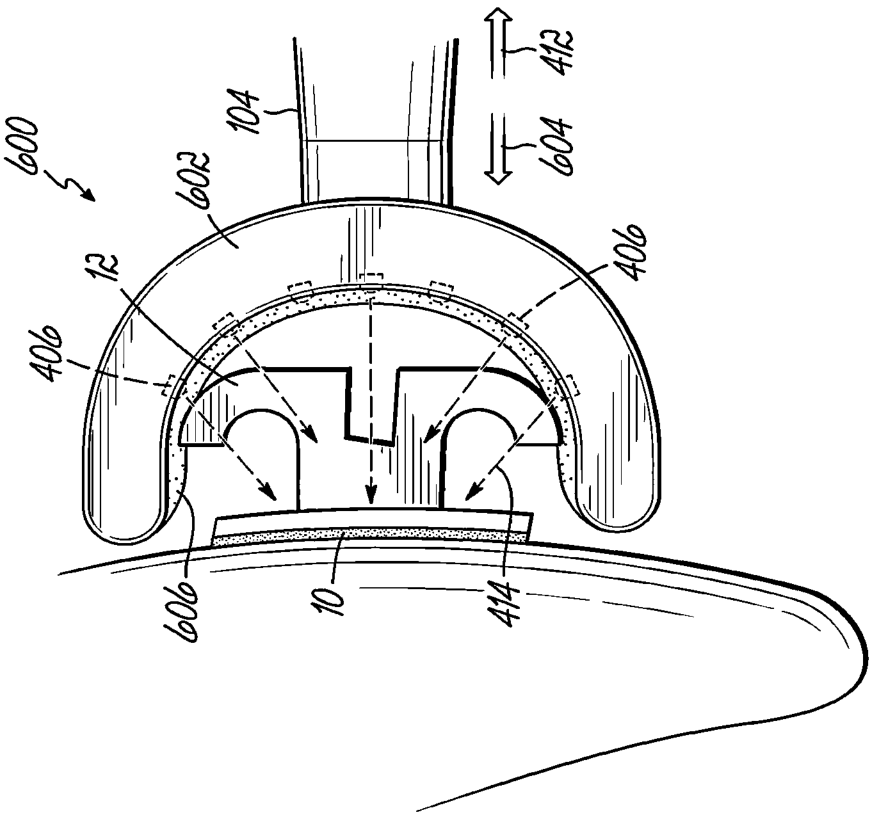
FIG. 18 is a schematic view of one embodiment of a light device.

With reference to FIG. 18, in one embodiment, a tip structure 600 is configured to remove a single orthodontic bracket 12. The tip structure 600 includes a U-shaped member 602 that may be forcibly inserted onto the bracket 12 in the direction of the arrow 604. The U-shaped member 602 may include liner 606 that frictionally engages the orthodontic bracket 12. Thus, insertion of the tip structure 600 along the direction of arrow 604 frictionally engages the U-shaped member 602 with the orthodontic bracket 12.

Following or during irradiation with light 414 from the light sources 406, the clinician may remove the orthodontic bracket in the direction of arrow 412 in a manner similar to that described above with regard to the tip structures 400 and 500. The clinician may pull on the bracket 12 to dislodge it from the tooth.

Unlike the tip structures described above, the tip structure 700 shown in FIGS. 20A and 20B contacts the archwire 20 while the archwire 20 is engaged in each orthodontic bracket 12. Pulling on the archwire 20 during irradiation of the adhesive 10 removes all of the brackets 12 connected to the archwire 20. To that end, in one embodiment, the tip structure 700 includes a plurality of C-shaped members 702 that each define a cavity 704. The cavity 704 receives the archwire 20. A pair of projections 712 produce an interference fit between the C-shaped member 702 and the archwire 20 so as to permit application of pulling forces on the archwire 20. The plurality of C-shaped members 702 are coupled together by a connector 706. The tip structure 700 may be removably coupled to a handle, such as handle 104. The number of C-shaped members 702 may be approximately the same as the number of orthodontic brackets 12 on the patient's arch. As shown, the C-shaped member 702 carries a plurality of light sources 708, which may be similar to the light sources 120 described above or different light sources. The light sources 708 may be oriented in the direction of the orthodontic bracket 12 that is situated between adjacent C-shaped members 702 during use of the tip structure 700.

During use, the clinician attaches each C-shaped member 702 to the archwire 20 by placing the archwire 20 in the cavity 704. This positions the C-shaped member 702 adjacent the orthodontic bracket 12. Activating the light sources 708 irradiates the adhesive 10 of the brackets 12 situated between adjacent C-shaped members 702. Once the adhesive 10 is sufficiently weakened, the clinician may pull the plurality of C-shaped members 702 in the direction generally indicated by the arrow 710 in FIG. 20B. Once the adhesive 10 releases each bracket, the clinician may pull an entire arch of brackets off the patient's teeth in a single process.

Furthermore, according to embodiments of the invention, the photocleavable moiety may enable reversible adhesion of the orthodontic adhesive system 10 to the tooth surfaces 22. The bonding process and the reversible adhesiveness may even be a type of fast curing (e.g., curing may occur during the few moments when the clinician presses the orthodontic device against the tooth with the catechol derivative-containing compound present on the tooth and the functional monomer present on the restorative part). In one embodiment, the adhesive system 10 may be activated and deactivated during bonding and debonding, respectively, with the light device described herein. Curing may include exposing the adhesive to blue light in one or more wavelengths from 450 nm to 495 nm. The adhesion to the tooth may be reversible in the sense that it can be bonded to the tooth and then debonded from the tooth at least twice. This may be useful for when the orthodontic bracket 12 or attachment 10 is initially improperly positioned. The orthodontic bracket 12 or attachment 10 may then be debonded by exposing the adhesive to wavelengths in the ultraviolet light spectrum, for example, from about 380 nm to about 450 nm. Once debonded, the orthodontic bracket 12 or attachment 10 may be reoriented and re-bonded to the tooth surface 22.

Thus, the adhesive and light devices described herein may facilitate an on-demand bonding and on-demand debonding process that permits easy repositioning of the orthodontic device. This may be referred to as a reusable adhesive system. Advantageously, orthodontic device placement may be perfected without concern that the adhesive polymerizes prior to proper positioning as the adhesive may be selectively bonded and debonded and then rebonded without addition of more adhesive. Clinically, the process of repositioning is tedious, thus embodiments of the adhesive described herein save repositioning time and present a significant shift in the standard of patient care. One or more brackets may be simultaneously bonded and debonded with the light devices disclosed herein.

In order to facilitate a more complete understanding of the embodiments of the invention, the following non-limiting examples are provided.

EXAMPLE

A primer solution of 7.5 wt. % 10-Methacryloxydecyl Dihydrogen Phosphate (MDP) that is modified to have a lower acid value (i.e., purified by removing HCl byproduct), 0.005 wt. % Catechol-methacrylate (CMA) (using eugenol as a backbone for the CMA), and 0.0075 wt. % butylated hydroxytoluene (BHT) in a balance of acetone was applied with a brush to a bovine tooth that was prepared by wiping it with a tissue. No other preparation techniques were used to prepare the surface of the tooth.

A debonding layer is formed from a second solution of 10 wt. % photocleavable bis-methacrylate, 0.01 wt. % N, N-di-methyl-amino-ethyl methacrylate (DMAEMA), 0.01 wt % camphoroquinone (CQ), and 0.001 wt % BHT in a balance of acetone was applied with a brush to the dried primer.

A Damon® Q metal bracket was bonded to the debonding layer with Grēngloo® adhesive and cured according to the manufacturer's directions.

Debonding of the metal bracket was achieved by exposure to 10 W UV light source at a wavelength of 395 nm in combination with a vibrating scaler operating at 24-32 kHz for about 30 seconds.

Debonding of a ceramic bracket was achieved at a 28 kHz of vibrational energy with simultaneous exposure to light at 940 nm with a power of 2.75 W in 34 seconds. For comparison, debonding was achieved with UV light at 365 nm and 3.08 W with 28 kHz in about 200 seconds.

Figure 21:
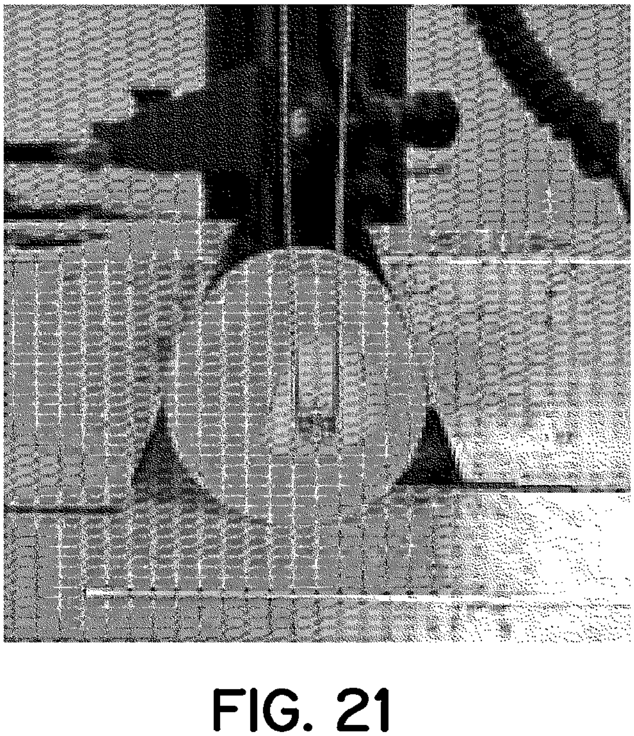
FIG. 21 is a photograph of a testing arrangement utilized to measure debonding force when debonding brackets from teeth.

In another example, 40 brackets were bonded to individual bovine teeth as set forth in the previous example. Twenty of the samples were debonded with an Instron® testing machine without irradiating the bond between the bracket in the tooth. The arrangement shown in FIG. 21 is utilized to debond the brackets from the teeth. As shown, tooth was encapsulated in epoxy with the bonded bracket exposed. A wire was looped around the bracket and attached to a grip on a cross head of the Instron® machine. With this arrangement, a shear load was produced on the adhesive. The average debond force measured was about 30 lbs force. Of the 20 samples, it is estimated that 90% of the adhesive remained on each of the teeth after the bracket debonded. Thus, a majority of the adhesive remained on each tooth.

The remaining 20 samples were irradiated for 1 minute at a distance of about 0.5 cm with an LED that produces a wavelength of 940 nm at 2,750 mW. The estimated bond area between the tooth and the orthodontic bracket was about 0.1 $cm^2$. Following that dosage, the arrangement shown in FIG. 21 was utilized to debond the brackets from the teeth. The average debond force measured was about 30 lbs force, however, all of the brackets debonded with the adhesive secured to the bracket. That is, there was no adhesive residue visible on any of the teeth for any of the 20 samples.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in any combination depending on the needs and preferences of the user.

What is claimed is:

1. A method of orthodontic treatment of a patient, the method comprising:

exposing an adhesive securing an orthodontic appliance to a tooth of the patient to incoherent actinic radiation that reduces a bond strength of at least a portion of the adhesive; and separating the orthodontic appliance from the tooth at the portion of the adhesive having reduced bond strength, wherein prior to exposing, the method further comprises:

applying the adhesive to the tooth and the orthodontic appliance;

affixing the orthodontic appliance to the tooth via the adhesive; and exposing the adhesive to a different spectrum of radiation from the incoherent actinic radiation to bond the orthodontic appliance to the tooth, wherein following exposing the adhesive to the incoherent actinic radiation, the method further comprises:

reorienting the orthodontic appliance relative to the tooth; and after reorienting, repeating the exposing of the adhesive to the different spectrum of radiation to bond the orthodontic appliance in a different orientation on the tooth.

2. The method of claim 1, wherein exposing the adhesive to incoherent actinic radiation includes exposing the adhesive to radiation in at least one of an IR spectrum, an NIR spectrum, and an UV spectrum.

3. The method of claim 1, wherein exposing the adhesive to incoherent actinic radiation includes exposing the adhesive to radiation in a blue portion of a visible light spectrum.

4. The method of claim 1, wherein exposing the adhesive to incoherent actinic radiation includes exposing the adhesive to radiation in an ultraviolet spectrum.

5. The method of claim 1, wherein exposing the adhesive to incoherent actinic radiation includes exposing the adhesive to radiation in an infrared spectrum.

6. The method of claim 1, wherein separating occurs during exposing the adhesive to incoherent actinic radiation.

7. The method of claim 1, wherein separating includes applying one or both of a tensile force or a shear force on the adhesive.

8. The method of claim 7, wherein applying includes pulling on the orthodontic appliance to separate the orthodontic appliance from the tooth.

9. The method of claim 1, wherein separating further comprises:

applying a mechanical debonding force to the orthodontic appliance.

10. The method of claim 9, wherein applying the mechanical debonding force and exposing the adhesive to incoherent actinic radiation are simultaneous.

11. The method of claim 9, wherein exposing the adhesive to incoherent actinic radiation includes exposing the adhesive to radiation in an infrared spectrum.

12. The method of claim 9, wherein exposing the adhesive to incoherent actinic radiation includes exposing the adhesive to radiation in a near infrared spectrum.

13. The method of claim 9, wherein exposing the adhesive to incoherent actinic radiation includes exposing the adhesive to radiation in a blue portion of a visible light spectrum.

14. The method of claim 9, wherein exposing the adhesive to incoherent actinic radiation includes exposing the adhesive to radiation in an ultraviolet spectrum.

15. The method of claim 1, wherein separating includes exposing the orthodontic appliance to ultrasonic vibration.

16. The method of claim 15, wherein exposing the adhesive to incoherent actinic radiation and exposing the orthodontic appliance to ultrasonic vibration are simultaneous.

17. The method of claim 16, wherein exposing the adhesive to incoherent actinic radiation includes exposing the adhesive to radiation in an infrared spectrum.

18. The method of claim 16, wherein exposing the adhesive to incoherent actinic radiation includes exposing the adhesive to radiation in a near infrared spectrum.

19. The method of claim 16, wherein exposing the adhesive to incoherent actinic radiation includes exposing the adhesive to radiation in a blue portion of a visible light spectrum.

20. The method of claim 16, wherein exposing the adhesive to incoherent actinic radiation includes exposing the adhesive to radiation in an ultraviolet spectrum.

21. The method of claim 1, wherein a plurality of individual orthodontic appliances are bonded to individual ones of the patient's teeth with the adhesive between individual ones of the orthodontic appliances and individual ones of the patient's teeth, wherein exposing the adhesive to incoherent actinic radiation reduces a bond strength of at least a portion of the adhesive bonding the individual ones of the orthodontic appliances to individual ones of the patient's teeth, and wherein separating includes separating each of the orthodontic appliances from each respective tooth at the portion of each of the plurality of individual adhesives having reduced bond strength.

22. The method of claim 21, wherein exposing the adhesive between individual ones of the orthodontic appliances and individual ones of the patient's teeth to the incoherent actinic radiation occurs simultaneously.

23. The method of claim 22, wherein separating each of the individual ones of the orthodontic appliances from respective individual ones of the patient's teeth occurs simultaneously.

24. The method of claim 21, wherein separating further comprises:

applying a mechanical debonding force to each of the individual ones of the orthodontic appliances.

25. The method of claim 24, wherein applying the mechanical debonding force and exposing the adhesive between individual ones of the orthodontic appliances and individual ones of the patient's teeth to the incoherent actinic radiation are simultaneous.

* * * * *